US006943182B2

(12) United States Patent
Guarnieri et al.

(10) Patent No.: US 6,943,182 B2
(45) Date of Patent: Sep. 13, 2005

(54) CYCLOPENTABENZOFURAN DERIVATIVES AND THEIR USE

(75) Inventors: Walter Guarnieri, Leverkusen (DE); Thomas Jaetsch, Cologne (DE); Andreas Schoop, Overath (DE); Jörg Baumgarten, Wuppertal (DE); Axel Kretschmer, Wuppertal (DE); Horst-Peter Antonicek, Bergisch-Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/160,385

(22) Filed: May 30, 2002

(65) Prior Publication Data

US 2003/0144334 A1 Jul. 31, 2003

Related U.S. Application Data

(63) Continuation of application No. 09/762,417, filed as application No. PCT/EP99/05472 on Jul. 29, 1999, now Pat. No. 6,420,393.

(30) Foreign Application Priority Data

Aug. 5, 1998 (DE) .......................... 198 35 324

(51) Int. Cl.[7] .................... A61K 31/443; A61K 31/343; C07D 405/04; C07D 307/93; A61P 29/00
(52) U.S. Cl. ...................... 514/337; 514/444; 514/464; 514/468; 546/284.1; 549/60; 549/78; 549/435; 549/458; 549/466
(58) Field of Search ............................ 549/60, 78, 435, 549/458, 466; 546/284.1; 514/337, 444, 464, 468, 449

(56) References Cited

U.S. PATENT DOCUMENTS

| 4,539,414 A | 9/1985 | King et al. .................. 549/458 |
| 5,274,167 A | 12/1993 | Lange et al. .................. 560/40 |
| 5,702,710 A | 12/1997 | Charpentier et al. ......... 424/401 |

FOREIGN PATENT DOCUMENTS

| EP | 0709382 | 1/1996 |
| WO | 9604284 | 2/1996 |
| WO | 9708161 | 6/1997 |

OTHER PUBLICATIONS

Adams C. Synthetic Communications, 1984, 14(10): 955–9.*
Gribble GW and Nutaitis CF. Organic Preparations and Procedures International (1985), 17(4–5), 317–320.*
Baldwin Jr., A. S., "The NF–κB and IκB Proteins: New Discoveries and Insights", Annu. Rev. Immunol., 14: 649–681 (1996).

Barnes, P. J.; Adcock, I. M., "NF–κB: A Pivotal Role in Asthma and a New Target for Therapy", TIPS, 18: 46–50 (Feb. 1997).

Baeuerle, P. A.; Henkel, T., "Function an Activation of NF–κB in the Immune System", Annu. Rev. Immunol., 12: 141–179 (1994).

Cui, B.; Chai, H.; Santisuk, T.; Reutrakul, V.; Farnsworth, N. R.; Cordell, G. A.; Pezzuto, J. M.; Kinghorn, A. D., "Novel Cytotoxic 1H–Cyclopenta[b]benzofuran Ligans from Aglaia elliptica", Tetrahedron, 53(52): 17625–17632 (1997).

Davey, A. E.; Schaeffer, M. J.; Taylor, R. J. K., "Synthesis of the Novel Anti–leukaemic Tetrahydrocyclopenta[b]benzofuran, Rocalamide and Related Synthetic Studies", J. Chem. Soc. Perkin Trans. 1, pp. 1657–2665 (1992).

Davey, A. E., Schaeffer, M. J., and Taylor, R. J. K., "Synthesis of the Novel Anti–leukaemic Tetrahydrocyclopenta[b]benzofuran, Rocaglamide", J. Chem. Soc. Commun., pp. 1137–1139 (1991).

Dumontet, V., Thoison, O., Omobuwajo, O. R., Martin, M.–T., Perromat, G., Chiaroni, A., Riche, C., Pais, M., and Sevenet, T., "New Nitrogenous and Aromatic Derivatives from Aglaia argentea and A. forbesii", Tetrahedron 52(20): 6931–6942 (1996).

Dieter Von, A.; Börner, B.; Grosser, R.; Lange, W., "Neue Chirale Stationäre Polyamid–Phasen für die Chromatographische Enantiomerentrennung", Angew. Chem., 103(12): 1685–1687 (1991).

Goldfeld, A. E.; Doyle, C.; Maniatis, T., "Human Tumor Necrosis Factor α Gene Regulation by Virus and Lipopolysaccharide", Proc. Natl. Acad. Sci. USA, 87: 9769–9773.

Güssregen, B.; Fuhr, M.; Nugroho, B. W.; Wray, V.; Witte, L.; Proksch, P., "New Insecticidal Rocaglamide Derivatives from Flowers of Aglaia odorata", Z. Naturforsch., C: Biosci., 52(5/6): 339–344 (1997).

Ishibashi, F.; Satasook, C.; Isman, M. B.; Towers, G. H. N., "Insecticidal 1H–Cyclopentatetrahydro[b]benzofurans from Aglaia odorata", Phytochemistry, 32(2): 307–310 (1993).

Lenardo, M.J.; Baltimore, D., "NF–κB: a Pleiotropic Mediator of Inducible and Tissue–Specific Gene Control", Cell, 58: 227–229 (1989).

(Continued)

Primary Examiner—Evelyn Mei Huang
(74) Attorney, Agent, or Firm—Susan M. Pellegrino

(57) ABSTRACT

The invention relates to cyclopentabenzofuran derivatives, process for their preparation, the use of cyclopentabenzofuran derivatives for the production of a medicament for the therapy of NF-κB-dependent diseases and medicaments which contain the cyclopentabenzofuran derivatives.

9 Claims, No Drawings

OTHER PUBLICATIONS

Loveys, B.; Milborrow, B. V., "Hydroxylation of Methyl Abscisate and the Formation of Three β–D–Glucosides", Phytochemistry, 31(1): 67–72 (1992).

Lu King, M.; Chiang, C.–C.; Ling, H.–C.; Fujita, E.; Ochiai, M.; McPhail, A. T., "X–Ray Crystal Structure of Rocaglamide, a Novel Antileukemic 1H–Cyclopenta[b]benzofuran from Aglaia elliptifolia", J. Chem. Soc., Chem. Commun., pp. 1150–1151 (1982).

Nugroho, B. W.; Edrada, R. A.; Güssregen, B.; Wray, V.; Witte, L.; Proksch, P., "Insecticidal Rocaglamide Derivatives from Aglaia Duppereana", Phytochemistry, 44(8): 1455–1461 (1997).

Oeth, P.; Parry, G. C. N.; Mackman, N., "Regulation of the Tissue Factor Gene in Human Monocytic Cells. Role of AP–1, NF–κB/Rel, and Sp1 Proteins in Uninduced and Lipopolysacharide–Induced Expression", Arteriosclerosis, Thrombosis, and Vascular Biology, 17(2): 365–374 (Feb. 1997).

Ohse, T.; Ohba, S.; Yamamoto, T.; Koyano, T.; Umezawa, K., "Cyclopentabenzofuran Lignan Protein Synthesis Inhibitors from Aglaia odorata", J. Nat. Prod., 59: 650–652 (1996).

Read, M. A.; Whitley, M. Z.; Gupta, S.; Pierce, J. W.; Best, J.; Davis, R. J.; Collins, T., "Tumor Necrosis Factor α–Induced E–Selectin Expression is Activated by the Nuclear Factor–κB and c–JUN N–terminal Kinase/p38 Mitogen–activated Protein Kinase Pathways", J. Biol. Chem., 272(5): 2753–2761 (Jan. 1997).

Satasook, C.; Isman, M. B.; Wiriyachitra, P., "Activity of Rocaglamide, an Insecticidal Natural Product, Against the Variegated Cutworm, Peridroma saucia (Lepidoptera: Noctuidae)", Pestic. Sci., 36: 53–58 (1992).

Transfection of Mammalian Cells in Culture, L. G. Davis et al., Basic Methods in Molecular Biology, Elsevier Sci. Publishing Co., New York (1986).

Greene, T. W.; Wuts, P. G. M., Protective Groups in Organic Synthesis, $2^{nd}$ Ed., John Wiley & Sons, New York (1991).

* cited by examiner

CYCLOPENTABENZOFURAN DERIVATIVES AND THEIR USE

This application is a continuing application of U.S. Ser. No. 09/762,417 filed Mar. 26, 2001, now U.S. Pat. No. 6,420,393.

The invention relates to cyclopentabenzofuran derivatives, processes for their preparation, the use of cyclopentabenzofuran derivatives for the production of a medicament for the therapy of NF-κB-dependent diseases and medicaments which contain the cyclopentabenzofuran derivatives.

Extracts of the plant *Aglaia elliptifolia* exhibit antileukemic properties. The first active compound identified was a dihydrocyclopentabenzofuranol derivative called rocaglamide (J. Chem. Soc., Chem. Commun. 1982, 1150; U.S. Pat. No. 4,539,414). After this, several studies appeared on synthesis experiments which were finally also successful (J. Chem. Soc., Chem. Commun. 1991, 1137). Only 10 years after the isolation of rocaglamide were its insecticidal properties described (Pestic. Sci 36, 53 (1992) and Phytochemistry 32, 67 (1993)) and after that in another species, *Aglaia odorata,* another three derivatives only differing in one substituent were found (Phytochemistry 32, 307 (1993)). Later, for example, from the species *Aglaia roxburghiana,* the first four fused derivatives of rocaglamide were isolated (WO 96/04284), then numerous further new derivatives and their pharmacological properties were described (cf., for example, J. Nat. Prod. 59, 650 (1996); Tetrahedron 52, 6931 (1996); Phytochemistry 44, 1455 (1997); Phytochemistry 45 1579 (1997); Z. Naturforsch., C: Biosci. 52, Tetrahedron 52, 17625 (1997); B. W. Nugroho, Thesis, Bayer. Julius-Maximilian Univ. Würzburg, 1997); WO 97/08161 A1).

An important step in many inflammatory processes is the translocation of the protein "nuclear factor kappa B", in brief NF-κB, into the cell nucleus and the stimulation of the expression of the genes caused thereby, whose products are responsible for inflammatory reactions (Trends Pharmacol. Sci. 18, 46 (1997)). For example, in asthma the nonbeneficial, excessive (non self-limiting) production of these proteins is responsible for the intensification and maintenance of the inflammatory process and the unpleasant to life-threatening symptoms of this disease associated therewith.

Because the long-term treatment with glucocorticoids corresponding to the present state of the art is affected by some disadvantages, NF-κB is seen as a compelling target for the development of new antiinflammatory active compounds against asthma.

It has now been found that the cyclopentabenzofuran derivatives of the formula (I)

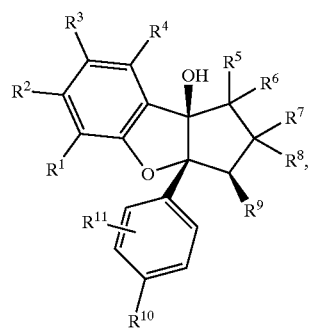

(I)

in which
$R^1$ and $R^3$ independently of one another in each case represent hydrogen, halogen or alkyl,
$R^2$ and $R^4$ independently of one another in each case represent halogen, alkyl or optionally substituted alkoxy,
$R^5$ represents hydroxyl, alkylamino or the radical —$NR^{12}$—$CHR^{13}$—$COOR^{14}$, in which
  $R^{12}$ represents hydrogen or alkyl,
  $R^{13}$ represents one of the radicals of a natural or synthetic α-amino acid, where functional groups can optionally be present in protected form, or
  $R^{12}$ and $R^{13}$ together represent —$(CH_2)_3$— and —$(CH_2)_4$—, and
  $R^{14}$ represents alkyl, benzyl or another C-terminal protective group,
$R^6$ represents hydrogen or
$R^5$ and $R^6$ together represent oxygen (oxo),
$R^7$ and $R^8$ in each case represent hydrogen,
$R^9$ represents optionally substituted phenyl or hetaryl,
$R^{10}$ represents hydrogen, halogen, alkyl or alkoxy and
$R^{11}$ represents hydrogen, halogen or alkyl,
and their salts
are suitable as inhibitors of nuclear factor kappa B (NF-κB)-mediated gene expression for the therapy of pathophysiological processes.

Depending on the nature of the substituents, the compounds of the formula (I) can also be present as geometrical and/or optical isomers or isomer mixtures, in different compositions, which can optionally be separated in a customary manner. Both the pure isomers and the isomer mixtures, their preparation and use, and compositions containing these are a subject of the present invention. Below, for the sake of simplicity, however, compounds of formula (I) are always referred to, although both the pure compounds and optionally also mixtures having different proportions of isomeric compounds are intended.

If, in a structural formula, the number of diastereomers is restricted by fixing the configuration on at least two chiral centers then, if not stated otherwise, in principle also the other enantiomers (mirror image) are intended.

The compounds according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acid or sulfonic acids. Particularly preferred salts are, for example, those with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Those particularly preferred are, for example, sodium, potassium, magnesium or calcium salts, and also ammonium salts, which are derived from ammonia, or organic amines, such as ethylamine, di- or triethylamine, di- or triethanolamine, dicyclohexylamine, dimethylaminoethanol, arginine, lysine, ethylenediamine or 2-phenylethylamine.

Formula (I) provides a general definition of the substances utilizable according to the invention. Preferred substituents or ranges of the radicals listed in the formulae above and below are explained in the following.

$R^1$ and $R^3$ independently of one another preferably in each case represent hydrogen, fluorine, chlorine, bromine or $C_1$–$C_6$-alkyl.

$R^2$ and $R^4$ independently of one another preferably in each case represent fluorine, chlorine, bromine, $C_1$–$C_6$-alkyl or $C_1$–$C_4$-alkoxy optionally substituted by fluorine or chlorine.

$R^5$ preferably represents hydroxyl, $C_1$–$C_4$-alkylamino or the radical —$NR^{12}$—$CHR^{13}$—$COOR^{14}$.

$R^6$ preferably represents hydrogen.

$R^5$ and $R^6$ also preferably together represent oxygen (oxo).

$R^7$ and $R^8$ preferably in each case represent hydrogen.

$R^9$ preferably represents phenyl, methylenedioxyphenyl or 5- or 6-membered hetaryl having 1 or 2 heteroatoms from the series consisting of nitrogen, oxygen and sulfur which in each case can optionally be substituted up to four times by substituents of the group: halogen, $C_1$–$C_6$-alkyl, hydroxyl, $C_1$–$C_4$-alkoxy, $C_1$–$C_4$-alkylthio, $C_1$–$C_4$-alkylcarbonyl, phenyl, phenoxy, hetaryl, hetaryloxy, $C_1$–$C_4$-alkyl substituted by fluorine or chlorine, $C_1$–$C_4$-alkoxy substituted by fluorine or chlorine, $C_1$–$C_4$-alkylthio substituted by fluorine or chlorine, $C_1$–$C_4$-alkylcarbonyl substituted by fluorine or chlorine.

$R^{10}$ preferably represents hydrogen, fluorine, chlorine, $C_1$–$C_6$-alkyl or $C_1$–$C_6$-alkoxy.

$R^{11}$ preferably represents for hydrogen, fluorine, chlorine, bromine or $C_1$–$C_6$-alkyl.

$R^{12}$ preferably represents hydrogen or $C_1$–$C_4$-alkyl.

$R^{13}$ preferably represents hydrogen, $C_1$–$C_4$-alkyl optionally substituted by amino or hydroxyl or represents mercaptomethyl, methylthioethyl, carboxymethyl, carboxyethyl, carbamoylmethyl, carbamoylethyl, guanidinopropyl or represents phenyl or benzyl optionally substituted by amino, nitro, halogen, hydroxyl or methoxy or represents naphthylmethyl, indolylmethyl, imidazolylmethyl, triazolylmethyl or pyridylmethyl, where functional groups can optionally be present in protected form.

$R^{12}$ and $R^{13}$ also preferably together represent —$(CH_2)_3$— or —$(CH_2)_4$—.

$R^{14}$ preferably represents $C_1$–$C_6$-alkyl, benzyl or another C-terminal protected group.

$R^1$ and $R^3$ independently of one another particularly preferably in each case represent hydrogen, fluorine, chlorine, bromine, methyl or ethyl.

$R^2$ and $R^4$ independently of one another particularly preferably in each case represent fluorine, chlorine, bromine, $C_1$–$C_4$-alkyl or methoxy or ethoxy optionally substituted by fluorine or chlorine.

$R^5$ particularly preferably represents hydroxyl, $C_1$–$C_4$-alkylamino or the radical —$NR^{12}$—$CHR^{13}$—$COOR^{14}$.

$R^6$ particularly preferably represents hydrogen.

$R^5$ and $R^6$ also particularly preferably together represent oxygen (oxo).

$R^7$ and $R^8$ particularly preferably in each case represent hydrogen.

$R^9$ particularly preferably represents phenyl, methylenedioxyphenyl or 5- or 6-membered hetaryl having 1 or 2 heteroatoms from the series consisting of nitrogen, oxygen and sulfur, which in each case can optionally be substituted up to 3 times by substituents of the group: fluorine, chlorine, bromine, iodine, $C_1$–$C_4$-alkyl, hydroxyl, $C_1$–$C_4$-alkoxy, $C_1$–$C_4$-alkylthio, $C_2$–$C_4$-alkylcarbonyl, phenyl, phenoxy, furyl, thienyl, pyrrolyl, thiazolyl, pyridyl, furyloxy, thienyloxy, pyrrolyloxy, thiazolyloxy, pyridyloxy, $C_1$–$C_4$-alkyl substituted by fluorine or chlorine, $C_1$–$C_3$-alkoxy substituted by fluorine or chlorine, $C_1$–$C_3$-alkylthio substituted by fluorine or chlorine, $C_1$–$C_4$-alkylcarbonyl substituted by fluorine or chlorine.

$R^{10}$ particularly preferably represents hydrogen, fluorine, $C_1$–$C_4$-alkyl or $C_1$–$C_4$-alkoxy.

$R^{11}$ particularly preferably represents hydrogen, fluorine, chlorine, bromine or $C_1$–$C_4$-alkyl.

$R^{12}$ particularly preferably represents hydrogen or methyl.

$R^{13}$ particularly preferably represents hydrogen, methyl, iso-propyl, iso-butyl, sec-butyl, hydroxymethyl, 1-hydroxyethyl, mercaptomethyl, 2-methylthioethyl, 3-aminopropyl, 4-aminobutyl, carboxymethyl, 2-carboxyethyl, carbamoylmethyl, 2-carbamoylethyl, 3-guanidinopropyl, phenyl, benzyl, 4-hydroxybenzyl, 4-methoxybenzyl, 2-nitrobenzyl, 3-nitrobenzyl, 4-nitrobenzyl, 2-aminobenzyl, 3-aminobenzyl, 4-aminobenzyl, 3,4-dichlorobenzyl, 4-iodobenzyl, α-naphthylmethyl, β-naphthylmethyl 3-indolylmethyl, 4-imidazolylmethyl, 1,2,3-triazol-1-ylmethyl, 1,2,4-triazol-1-ylmethyl, 2-pyridylmethyl or 4-pyridylmethyl, where functional groups can optionally be present in protected form.

$R^{12}$ and $R^{13}$ also particularly preferably together represent —$(CH_2)_3$— or —$(CH_2)_4$—.

$R^{14}$ particularly preferably represents $C_1$–$C_4$-alkyl, benzyl or another C-terminal protective group.

$R^1$ and $R^3$ very particularly preferably in each case represent hydrogen, chlorine or bromine.

$R^2$ and $R^4$ very particularly preferably in each case represent methoxy, ethoxy, trifluoromethoxy, difluoromethoxy, chlorodifluoromethoxy, 2-chloro-1,1,2-trifluoroethoxy, 1,1,2-trifluoroethoxy, 1,1,2,2-tetrafluoroethoxy, 2,2,2-trichloro-1,1-difluoromethoxy or 1,1-difluoroethoxy, in particular methoxy or ethoxy.

$R^5$ very particularly preferably represents hydroxyl, methylamino, ethylamino, n-propylamino, isopropylamino, n-butylamino, isobutylamino, sec-butylamino, tert-butylamino or the radical —$NR^{12}$—$CHR^{13}$—$COOR^{14}$.

$R^6$ very particularly preferably represents hydrogen.

$R^5$ and $R^6$ also very particularly preferably together represent oxygen (oxo).

$R^7$ and $R^8$ very particularly preferably in each case represent hydrogen.

$R^9$ very particularly preferably represent phenyl, methylenedioxyphenyl, furyl, thienyl, pyrrolyl, oxazolyl, isoxazolyl, thiazolyl or pyridyl, which in each case can optionally be monosubstituted or disubstituted by substituents of the group: fluorine, chlorine, bromine, iodine, methyl, ethyl, n-propyl, isopropyl, n-butyl, isobutyl, sec-butyl, tert-butyl, trifluoromethyl, difluoromethyl, chlorodifluoromethyl, 2-chloro-1,1,2-trifluoroethyl, 1,1,2-trifluoroethyl, 1,1,2,2-tetrafluoroethyl, 1,1-difluoro-2,2,2-trichloroethyl, 2,2,2-trifluoroethyl, 1,1,2,3,3,3-hexafluoropropyl, 2,2,3,3-tetrafluoropropyl, 2,2,3,3,3-pentafluoropropyl, hydroxyl, methoxy, ethoxy, n-propoxy, isopropoxy, n-butoxy, isobutoxy, sec-butoxy, tert-butoxy, trifluoromethoxy, difluoromethoxy, chlorodifluoromethoxy, 2-chloro-1,1,2-trifluoroethoxy, 1,1,2-trifluoroethoxy, 1,1,2,2-tetrafluoroethoxy, 2,2,2-trichloro-1,1-difluoromethoxy, 1,1-difluoroethoxy, methylthio, ethylthio, trifluoromethylthio, 1,1-difluoroethylthio, 2,2,2-trifluoroethylthio, phenyl, phenoxy, acetyl, propionyl, propylcarbonyl, butylcarbonyl or 2-methylpropylcarbonyl.

$R^{10}$ very particularly preferably represents hydrogen, fluorine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy or tert-butoxy.

$R^{11}$ very particularly preferably represents hydrogen, fluorine, chlorine, bromine, methyl, ethyl, n-propyl, isopropyl, n-butyl, isobutyl, sec-butyl or tert-butyl.

$R^{12}$ very particularly preferably represents hydrogen.

$R^{13}$ very particularly preferably represents hydrogen, methyl, iso-propyl, iso-butyl, sec-butyl, hydroxymethyl, 1-hydroxyethyl, mercaptomethyl, 2-methylthioethyl, 3-aminopropyl, 4-aminobutyl, carboxymethyl, 2-carboxyethyl, carbamoylmethyl, 2-carbamoylethyl, 3-guanidinopropyl, phenyl, benzyl, 4-hydroxybenzyl, 3-indolylmethyl or 4-imidazolylmethyl.

$R^{14}$ very particularly preferably represents methyl, ethyl, n-propyl, isopropyl, n-butyl, isobutyl, sec-butyl, tert-butyl or benzyl.

The abovementioned general radical definitions and explanations or radical definitions and explanations mentioned in preferred ranges can be combined with one another in any desired manner, i.e. even between the respective ranges and preferred ranges. They apply correspondingly to the final products and also to the precursors and intermediates.

Preferred compounds of the formula (I) according to the invention are those in which a combination of the meanings (preferably) mentioned above as preferred is present.

Particularly preferred compounds of the formula (I) according to the invention are those in which a combination of the meanings mentioned above as particularly preferred is present.

Very particularly preferred compounds of the formula (I) according to the invention are those in which a combination of the meanings mentioned as very particularly preferred is present.

According to a second aspect, cyclopentabenzofuran derivatives of the formula (I) which can be used according to the invention are those in which $R^1$ and $R^3$ independently of one another in each case represent hydrogen, halogen or alkyl, $R^2$ and $R^4$ independently of one another in each case represent halogen, alkyl or optionally substituted alkoxy, $R^5$ represents hydroxyl, alkylamino or the radical —$NR^{12}$—$CHR^{13}$—$COOR^{14}$, in which $R^{12}$ represents hydrogen or alkyl, $R^{13}$ represents one of the radicals of a natural or synthetic a-amino acid, where functional groups can optionally be present in protected form, or $R^{12}$ and $R^{13}$ together represent —$(CH_2)_3$— and —$(CH_2)_4$—, and $R^{14}$ represents alkyl, benzyl or another C-terminal protective group, $R^6$ represents hydrogen or $R^5$ and $R^6$ together represent oxygen (oxo), $R^7$ and $R^8$ in each case represent hydrogen, $R^9$ represents optionally substituted phenyl or hetaryl, $R^{10}$ represents hydrogen, alkyl or alkoxy and $R^{11}$ represents hydrogen, halogen or alkyl According to the second aspect of the invention, compounds of the formula (I) are preferred in which $R^1$ and $R^3$ in each case represent hydrogen, fluorine, chlorine, bromine, methyl or ethyl, $R^2$ and $R^4$ in each case represent methoxy, ethoxy, trifluoromethoxy, difluoromethoxy, chlorodifluoromethoxy, 2-chloro-1,1,2-trifluoroethoxy, 1,1,2-trifluoroethoxy, 1,1,2,2-tetrafluoroethoxy, 2,2,2-trichloro-1,1-difluoromethoxy or 1,1-difluoroethoxy, $R^5$ represents hydroxyl, methylamino, ethylamino, n-propylamino, isopropylamino, n-butylamino, isobutylamino, sec-butylamino, tert-butylamino or the radical —$NR^{12}$—$CHR^{13}$—$COOR^{14}$, $R^6$ represents hydrogen, or $R^5$ and $R^6$ together represent oxygen (oxo), $R^7$ and $R^8$ in each case represent hydrogen, $R^9$ represents phenyl, methylenedioxyphenyl, furyl, thienyl, pyrrolyl, oxazolyl, isoxazolyl, thiazolyl or pyridyl, which is optionally monosubstituted or disubstituted by fluorine, chlorine, bromine, iodine, methyl, ethyl, n-propyl, isopropyl, n-butyl, isobutyl, sec-butyl, tert-butyl, trifluoromethyl, difluoromethyl, chlorodifluoromethyl, 2-chloro-1,1,2-trifluoroethyl, 1,1,2-trifluoroethyl, 1,1,2,2-tetrafluoroethyl, 1,1-difluoro-2,2,2-trichloroethyl, 2,2,2-trifluoroethyl, 1,1,2,3,3,3-hexafluoropropyl, 2,2,3,3-tetrafluoropropyl, 2,2,3,3,3-pentafluoropropyl, hydroxyl, methoxy, ethoxy, n-propoxy, isopropoxy, n-butoxy, isobutoxy, sec-butoxy, tert-butoxy, trifluoromethoxy, difluoromethoxy, chlorodifluoromethoxy, 2-chloro-1,1,2-trifluoroethoxy, 1,1,2-trifluoroethoxy, 1,1,2,2-tetrafluoroethoxy, 2,2,2-trichloro-1,1-difluoromethoxy or 1,1-difluoroethoxy, $R^{10}$ represents hydrogen, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy or tert-butoxy, $R^{11}$ represents hydrogen, fluorine, chlorine, bromine, methyl, ethyl, n-propyl, isopropyl, n-butyl, isobutyl, sec-butyl or tert-butyl, $R^{12}$ represents hydrogen, $R^{13}$ represents hydrogen, methyl, iso-propyl, iso-butyl, sec-butyl, hydroxymethyl, 1-hydroxyethyl, mercaptomethyl, 2-methylthioethyl, 3-aminopropyl, 4-aminobutyl, carboxymethyl, 2-carboxyethyl, carbamoylmethyl, 2-carbamoylethyl, 3-guanidinopropyl, phenyl, benzyl, 4-hydroxybenzyl, 3-indolylmethyl or 4-imidazolylmethyl, and $R^{14}$ represents methyl, ethyl, n-propyl, isopropyl, n-butyl, isobutyl, sec-butyl, tert-butyl, benzyl or another C-terminal protective group.

Saturated or unsaturated hydrocarbon radicals such as alkyl or alkenyl can as far as possible in each case be straight-chain or branched, even in combination with heteroatoms, such as in alkoxy.

Optionally substituted radicals can be monosubstituted or polysubstituted, where in the case of polysubstitution the substituents can be identical or different.

In the context of the invention hetaryl in general represents an aromatic optionally benzo-fused 5- to 7-membered, preferably 5- to 6-membered, heterocycle, which can contain up to 3 heteroatoms from the series consisting of S, N and/or O. Examples which may be mentioned are: indolyl, isoquinolyl, quinolyl, benzo[b]thiophene, benzo[b]furanyl, pyridyl, thienyl, furyl, pyrrolyl, thiazolyl, oxazolyl, isoxazolyl, imidazolyl, morpholinyl or piperidyl. Furyl, pyrrolyl, oxazolyl, isoxazolyl, thiazolyl, pyridyl and thienyl are preferred.

The protective groups known from peptide chemistry are mentioned, for example, in T. W. Greene, P. G. M. Wuts, Protective Groups in Organic Synthesis, $2^{nd}$ Ed., John Wiley & Sons, New York 1991. Examples of suitable protective groups are $C_1$–$C_4$-alkyl and benzyl in particular for hydroxyl or carboxyl groups (C-terminal protective groups); acetyl, trifluoroacetyl, trichloroacetyl, benzoyl, phenylacetyl, tertbutoxycarbonyl (Boc), benzyloxycarbonyl, (Cbz), (9-fluorenyl)methoxycarbonyl (Fmoc) and benzyl in particular for hydroxyl and amino groups (N-terminal protective groups).

Of these, those particularly preferred are tert-butyl, benzyl, acetyl, Boc and Cbz.

The abovementioned substances of the formula (I) which can be used according to the invention are new with the exception of 3,3a-dihydro-6,8-dimethoxy-3a-(4-methoxyphenyl)-3-phenyl-1H-cyclopenta[b]benzofuran-1,8b(2H)-diol and 2,3,3a,8b-tetrahydro-8b-hydroxy-6,8-dimethoxy-3a-(4-methoxyphenyl)-3-phenyl-1H-cyclopenta[b]benzofuran-1-one (cf. J. Chem. Soc., chem. Commun. 1991, 1137; J. Chem. soc. Perk. Trans. 1, 1992, 2657).

It has furthermore been found that the new compounds of the formula (I) can be obtained by one of the processes described below.

A) cis-Dihydrocyclopentabenzofurandiols of the Formula (I-a)

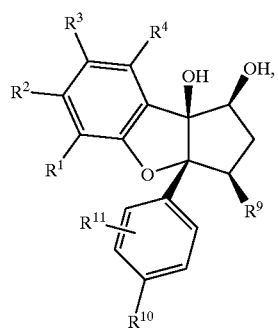

(I-a)

in which
  $R^1$, $R^2$, $R^3$, $R^4$, $R^9$, $R^{10}$ and $R^{11}$ have the meanings indicated above,
can be prepared by subjecting ketoaldehydes of the formula (II-a)

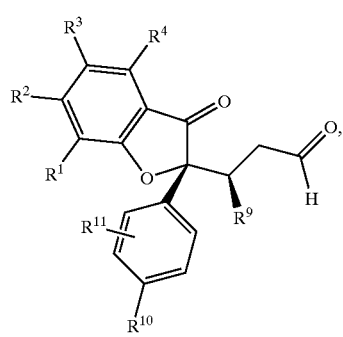

(II-a)

in which
  $R^1$, $R^2$, $R^3$, $R^4$, $R^9$, $R^{10}$ and $R^{11}$ have the meanings indicated above,
to reductive cyclization.

B) Tetrahydrocyclopentabenzofuranones of the Formula (I-b)

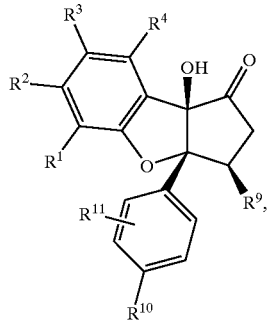

(I-b)

in which
  $R^1$, $R^2$, $R^3$, $R^4$, $R^9$, $R^{10}$ and $R^{11}$ have the meanings indicated above,
can be prepared by
oxidizing dihydrocyclopentabenzofurandiols of the formula (I-a)

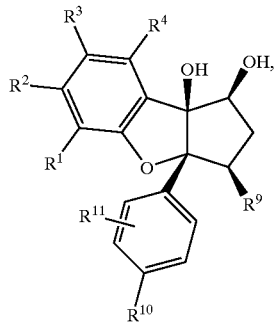

(I-a)

in which
  $R^1$, $R^2$, $R^3$, $R^4$, $R^9$, $R^{10}$ and $R^{11}$ have the meanings indicated above.

C) trans-Dihydrocyclopentabenzofurandiols of the Formula (I-c)

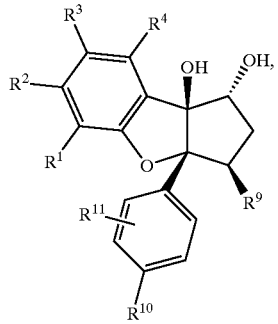

(I-c)

in which
  $R^1$, $R^2$, $R^3$, $R^4$, $R^9$, $R^{10}$ and $R^{11}$ have the meanings indicated above,
can be prepared by
reducing tetrahydrocyclopentabenzofuranones of the formula (I-b)

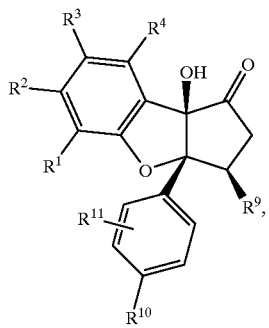

(I-b)

in which
R$^1$, R$^2$, R$^3$, R$^4$, R$^9$, R$^{10}$ and R$^{11}$ have the meanings indicated above,
with alkali metal or tetraalkylammonium acyloxyborohydrides.

D) Cyclopentabenzofuran Derivatives of the Formula (I-d)

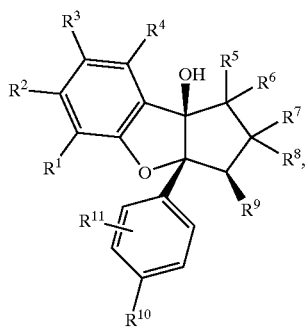

(I-d)

in which
R$^1$ to R$^{11}$ have the meanings indicated above, with the restriction that at least one of the radicals R$^1$, R$^3$ and R$^{11}$ represents halogen or alkyl,
can be prepared by introducing this or these radicals by electrophilic aromatic substitution of compounds of the formula (I) indicated above, in which the radical or radicals to be substituted represent(s) hydrogen.

E) Cyclopentabenzofuran Derivatives of the Formula (I-e)

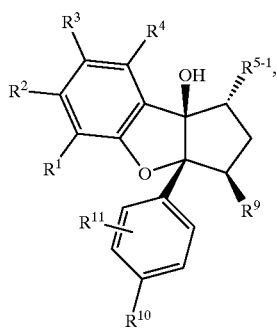

(I-e)

in which
R$^1$ to R$^4$ and R$^9$ to R$^{11}$ have the meanings indicated above and
R$^{5-1}$ represents alkylamino or the radical —NR$^{12}$—CHR$^{13}$—COOR$^{14}$, in which R$^{12}$, R$^{13}$ and R$^{14}$ have the meanings indicated above,
can be prepared by
reacting tetrahydrocyclopentabenzofuranones of the formula (I-b)

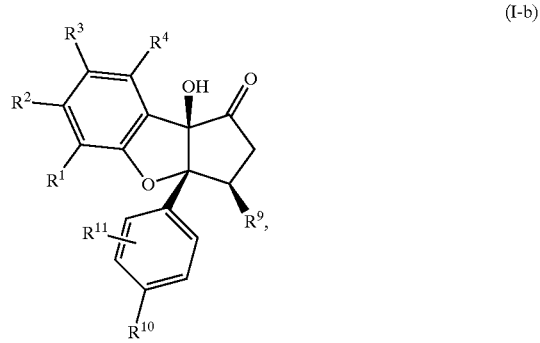

(I-b)

in which
R$^1$ to R$^4$ and R$^9$ to R$^{11}$ have the meanings indicated above,
with primary amines or amino acid derivatives of the formula (III)

$$H-R^{5-1} \qquad (III),$$

in which
R$^{5-1}$ represents alkylamino or the radical —NR$^{12}$—CHR$^{13}$—COOR$^{14}$, in which
R$^{12}$, R$^{13}$ and R$^{14}$ have the meanings indicated above,
in the presence of a reducing agent.

If, for example, 2,3-dihydro-4,6-diethoxy-2-(4-methoxyphenyl)-3-oxo-β-phenyl-2-benzofuranpropanal is used as a starting substance, the successive reaction courses of the processes (A), (B) and (C) according to the invention here can be shown by the following equation:

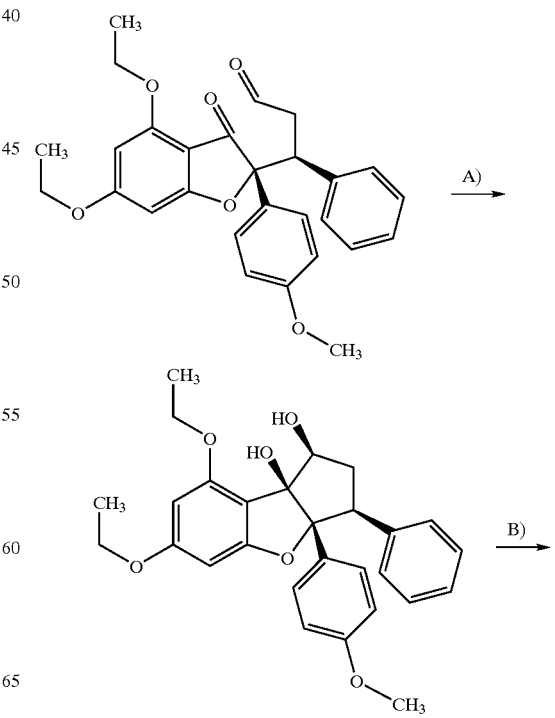

-continued

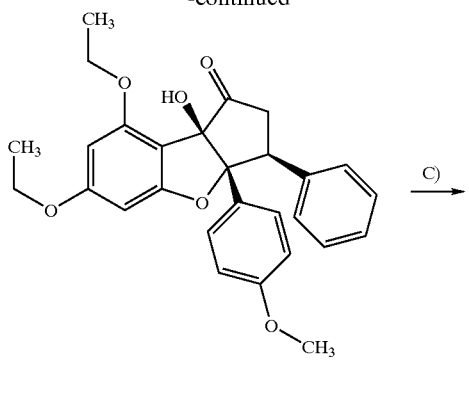

If, for example, 3,3a-dihydro-6,8-dimethoxy-3a-(4-methoxyphenyl)-3-phenyl-1H-cyclopenta[b]benzofuran-1,8b(2H)-diol is used as a starting compound and bromine-pyridine complex as a reagent, the reaction course of process (D) according to the invention can be shown by the following equation:

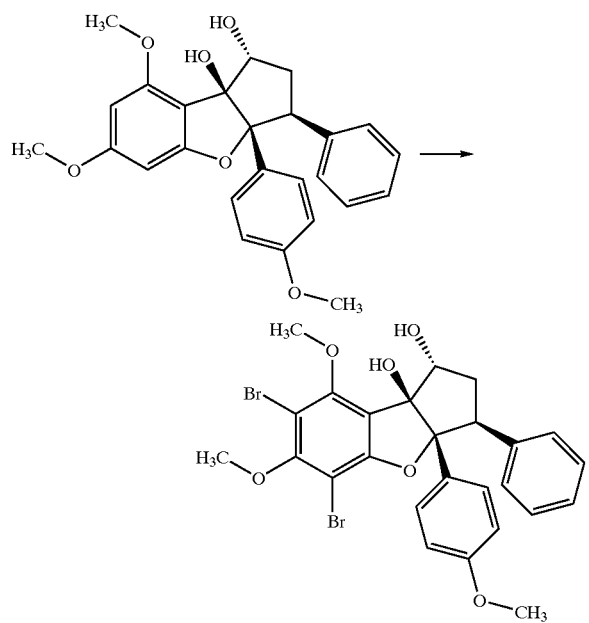

If, for example, 2,3,3a,8b-tetrahydro-8b-hydroxy-6,8-dimethoxy-3a-(4-methoxyphenyl)-3-phenyl-1H-cyclopenta[b]benzofuran-1-one and glycine methyl ester hydrochloride are used as starting substances and tetramethylammonium trisacetoxyborohydride in the presence of molecular sieve is used as a reagent, the reaction course of process (E) according to the invention can be shown by the following equation:

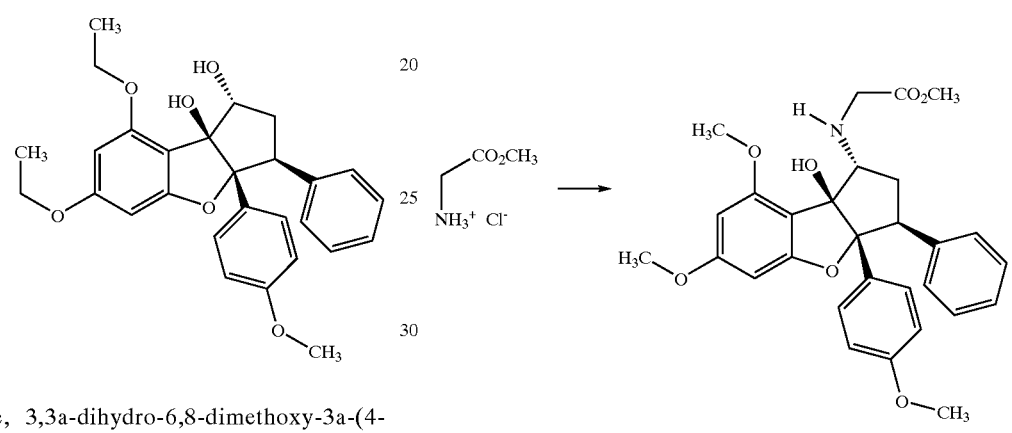

Formula (II-a) provides a general definition of the ketoaldehydes needed for carrying out process (A) according to the invention. In this formula, $R^1$ to $R^{11}$ preferably have those meanings which have already been mentioned as preferred in connection with the description of the cyclopentabenzofuran derivatives of the formula (I). The ketoaldehydes of the formula (II-a) and the other diastereomers of the formula (II-b) indicated further below are new with the exception of 2,3-dihydro-4,6-dimethoxy-2-(4-methoxyphenyl)-3-oxo-β-phenyl-2-benzofuranpropanal.

Ketoaldehydes of the formulae (II-a) and (II-b) can be prepared, for example, by adding benzofuranones of the formula (IV) to cinnamaldehyde or its heterocyclic analogs of the formula (V) in the presence of an acid-binding agent, such as benzyltrimethylammonium hydroxide solution or sodium methoxide and in the presence of a diluent, such as methanol or tert-butanol, according to the following reaction scheme:

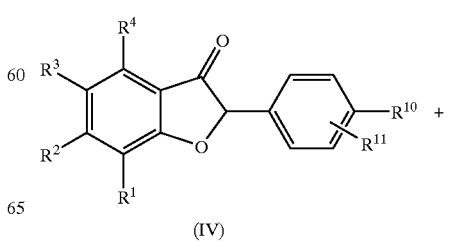

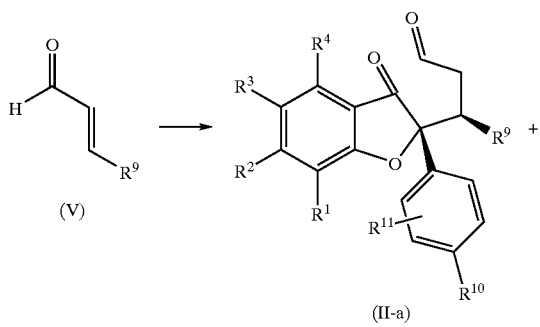

(V) → (II-a)

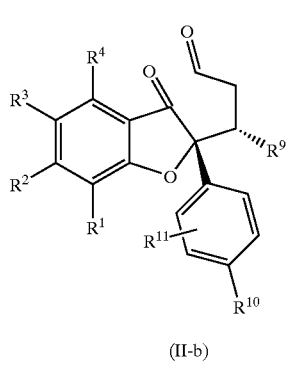

(II-b)

The diastereomers (II-a) and (II-b) can be separated by column chromatography according to customary methods.

The vinylogous arylaldehydes of the formula (V) are in some cases commercially obtainable, are known or can be prepared according to known methods.

Benzofuranones of the formula (IV) can be prepared, for example, by Hoesch reaction of cyanohydrins (cf. Chem. Soc. Perkin Trans. I, 1992, 2657) or preferably trimethylsilylcyanohydrins (cf. Preparation examples) of the formula (VI) of 4-substituted benzaldehydes, in which $R^{15}$ represents hydrogen or trimethylsilyl (TMS), with phenols of the formula (VII) according to the following reaction scheme:

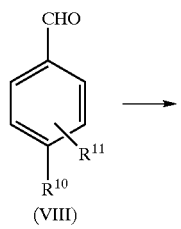

(VIII)

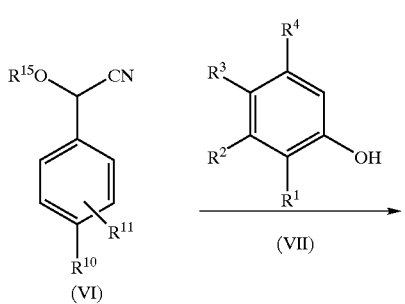

(VI)   (VII)

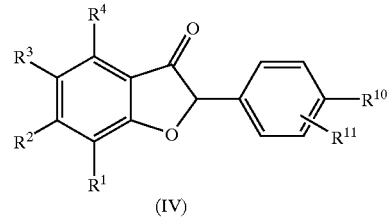

(IV)

The benzaldehydes of the formula (VIII) and phenols of the formula (VII) needed for this are generally known compounds of organic chemistry. The reaction of the benzaldehydes to give the cyanohydrins of the formula (VI) is carried out, for example, using sodium cyanide or trimethylsilyl cyanide according to known methods.

An example of the derivatization of the radicals $R^2$ and $R^4$ at the stage of the benzofuranone of the formula (IV) is alkylation (e.g. with diethyl sulfate/potassium carbonate) with subsequent cleavage of the resulting enol ether (e.g. with hydrochloric acid) according to the following reaction scheme:

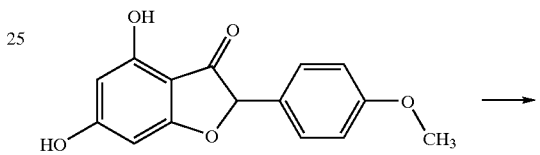

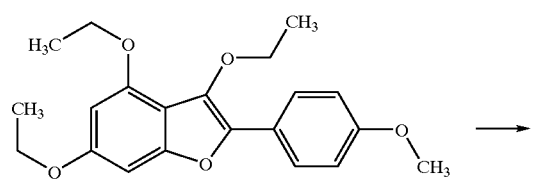

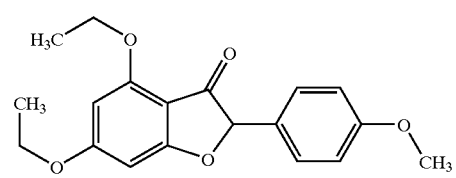

The dihydrocyclopentabenzofurandiols of the formula (I-a) needed for carrying out process (B) according to the invention are subsets of the compounds of the general formula (I) according to the invention and can be prepared, for example, by processes (A) or (D).

The tetrahydrocyclopentabenzofuranones of the formula (I-b) needed for carrying out processes (C) and (E) according to the invention are subsets of the compounds of the general formula (I) according to the invention and can be prepared, for example, by process (B) or (D).

The cyclopentabenzofurans needed for carrying out process (D) according to the invention are subsets of the compounds of the general formula (I) according to the invention and can be prepared, for example, by process (A), (C) or (E).

Formula (III) provides a general definition of the amines or amino acid derivatives needed for carrying out process (E) according to the invention. In this formula, $R^{5-1}$, if applicable, and also $R^{12}$ to $R^{14}$ preferably has those meanings which have already been mentioned as preferred for $R^5$ and also $R^{12}$ to $R^{14}$ in connection with the description of the cyclopentabenzofuran derivatives of the formula (I). The compounds of the formula (III) are mainly commercially obtainable or can be prepared by known methods of amino acid chemistry.

Process (A) according to the invention is carried out in the presence of a reducing agent. Samarium diiodide is preferably used for this purpose. Samarium diiodide can be employed as a solution (0.1 M) in THF or by reaction of samarium with 1,2-diiodoethane in solution.

Process (A) according to the invention is preferably carried out in the presence of a diluent. Those suitable are organic solvents such as, for example, aromatic hydrocarbons such as benzene or toluene or ethers such as tetrahydrofuran or dioxane.

Process (B) according to the invention is carried out as a Swern or Parikh-Doering oxidation. The reagents employed are, for example, dimethyl sulfoxide and oxalyl chloride/triethylamine or sulfur trioxide-pyridine complex and triethylamine.

Process (B) according to the invention is preferably carried out in the presence of a diluent. Those suitable are organic solvents such as, for example, ethers such as diethyl ether, tetrahydrofuran or dioxane or sulfoxides such as dimethyl sulfoxide.

The alkali metal or tetraalkylammonium acyloxyborohydrides needed for carrying out process (C) according to the invention are, for example, lithium, sodium, potassium or $C_1$–$C_4$-tetraalkylammonium salts of tris-$C_1$–$C_5$-(halogeno)alkyl-carbonyloxyborohydrides such as sodium trisacetoxyborohydride or tetramethylammonium trisacetoxyborohydride. The reducing agents can also be prepared in situ by employing, for example, lithium borohydride or sodium borohydride and the carboxylic acid corresponding to the desired acyl radical, such as acetic acid, trifluoroacetic acid or propionic acid.

Process (C) is preferably carried out in the presence of a diluent. Organic solvents are suitable for this purpose. The following may be mentioned by way of example: nitrites, such as acetonitrile, propionitrile, n- or i-butyronitrile or benzonitrile; carboxylic acids such as acetic acid or propionic acid.

Process (D) according to the invention comprises halogenations and Friedel-Crafts alkylations. Suitable reagents are, for example: chlorine, bromine, bromine-pyridine complex, N-bromosuccinimide, I,I-bis(trifluoroacetoxy)-iodobenzene, alkyl chlorides and alkyl bromides.

Process (D) is preferably carried out in the presence of a diluent. Organic solvents are suitable for this purpose. The following may be mentioned by way of example: aliphatic or alicyclic hydrocarbons, such as petroleum ether, hexane, heptane, cyclohexane, methylcyclohexane or decalin; halogenated hydrocarbons, such as chlorobenzene, dichlorobenzene, methylene chloride, chloroform, tetrachloromethane, dichloroethane, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; nitrites, such as acetonitrile, propionitrile, n- or i-butyronitrile or benzonitrile.

Process (D) is optionally carried out in the presence of a Lewis acid as a catalyst. Examples which may be mentioned are: iron (in brominations) iron chlorides and bromides, aluminum chloride and bromide, zinc chloride or boron trifluoride.

The reactions of the processes according to the invention can be carried out at normal pressure or at elevated pressure. They are preferably carried out at normal pressure. They are carried out, worked up and the reaction products are isolated according to generally customary, known methods. The final products are preferably purified by crystallization, chromatographic separation or by removal of the volatile constituents, optionally in vacuo (cf. also the Preparation examples).

The substances utilizable according to the invention are low molecular weight inhibitors which selectively inhibit nuclear factor kappa B (NF-κB)-mediated pathophysiological processes. NF-κB-mediated processes occur in inflammatory diseases, immunological disorders, septic shock, transplant rejection, radiation damage, reperfusion injuries after ischemia, stroke and cerebral trauma, thromboses, cirrhosis of the liver, asthma or in complex, chronic inflammatory disorders such as arteriosclerosis and multiple sclerosis.

The Pharmacological Action of Inhibitors of Nuclear Factor Kappa B

Nuclear factor kappa B (NF-κB) is a dimeric protein complex occurring in many tissue cells and in particular in blood cells. NF-κB takes on a particular role in the control of the expression of genes which have an NF-κB binding sequence (5'-GGGPuNNPyPyCC-3') in their promoter sequence. To this extent, NF-κB is a transcription factor. The physiological activity of NF-κB in the control of gene expression, however, is subject to a regulation principle, in which NF-κB is released from a complex with the protein IκB in order to be translocated as a transcription factor in the cell nucleus of gene activation. The regulation principle for the release of active NF-κB from a complex with the protein IκB is still not known in detail.

Likewise, it is not known how the formation of homodimeric and heterodimeric NF-κB protein complexes takes place. NF-κB acts on gene activation as a dimeric transcription factor. The dimerization can take place under the structurally related transcription factors Rel A, Rel B, c-Rel, p50 or p52, which form a family of transcription factor proteins. In the dimerization of the subunits to the NF-κB, there can also already be a regulation principle for the control of the genes later described in greater detail, which is still not known.

A crucial feature of NF-κB compared to other transcription factors is that NF-κB is a primary transcription factor. Primary transcription factors are already present in the cell in inactive (usually complex-bound) form and are released after an appropriate stimulus in order to be able to display their action very rapidly. Primary transcription factors are not first formed by the activation of the associated gene and subsequent transcription and translation.

This property of NF-κB, the formation of homodimeric or heterodimeric Rel proteins and the formation of an inactive protein complex with an IκB protein, offer very different points of attack for pharmacologically active substances than the points of attack of the de novo biosynthesis of transcription factors. For the sake of completeness, it may be mentioned that the genes for the formation of NF-κB (genes of the Rel family) and the genes for the formation of the IκB proteins (gene family comprising the genes for IκB-α, IκB-β, p105/IκB-γ, p100/IκB-δ, IκB-ε and others) for their part are of course also subject to regulation, which can be points of attack for pharmaceutically active substances. Thus it is known that the expression of the constitutively formed IκB proteins p105 and p100 is increased by stimuli which also activate NF-κB, such as tumour necrosis factor-α (TNF-α) or phorbol myristate acetate (PMA).

A regulation mechanism is described in the literature in which it is shown that the overexpression of IκB binds active NF-κB and thus inactivates it. This also applies if the NF-κB has already entered into a complex with the DNA (P. A. Baeuerle, T. Henkel, Annu. Rev. Immunol. 12, 141–179, 1994). From this it can be concluded that there are a number of specific points of attack in the biochemical function of NF-κB and IκB proteins which should make it possible to inhibit an undesirable, pathophysiological, NF-κB-dependent gene activation selectively.

A chemical compound which selectively inhibits the function of NF-κB or the function of IκB proteins or IκB genes to an increased extent should be able to be used as a pharmaceutical for the suppression of NF-κB-mediated disease processes.

Primarily, NF-κB can promote all pathophysiological processes in which genes are involved which have the NF-κB binding sequence in their promoter. Mainly, these are genes which play a crucial causal role in immunological complications, in inflammatory diseases, autoimmune disorders, septic shock, transplant rejection, thromboses or else alternatively in chronic inflammatory diseases such as arteriosclerosis, arthritis and rheumatism psoriasis.

NF-κB binding sequences contain, for example, the promoters of receptors of lymphoid cells (T-cell receptors), of MHCI and MHCII genes, of cell adhesion molecules (ELAM-1, VCAM-1, ICAM-1), of cytokines and growth factors (see also the following table). Furthermore, NF-κB binding sequences are found in the promoters of acute phase proteins (angiotensinogen, complement factors and others).

A chronically increased or acutely overshooting activation of the genes mentioned leads to various pathophysiological processes and syndromes.

The rapid and overshooting production of cytokines of the inflammatory reaction (TNFα, interleukin-2, interleukin-4, interleukin-6, interleukin-8 and others) and of the adhesion molecules (ELAM-1, VCAM-1) in leukocytes, in particular in macrophages and also in endothelial cells, is a causal feature of processes which often run a fatal course in the case of septic shock; or in the case of radiation damage and in the case of transplant rejection often leads to considerable complications. Inhibitors which prevent the NF-κB-mediated gene expression intervene very early in some diseases in the expression of pathophysiological changes and can therefore be a very effective therapeutic principle. An example is also NF-κB inhibitors for diseases which are to be attributed to an overexpression of acute-phase proteins. An undesirable overexpression of acute-phase proteins can cause a complex general reaction in which tissue damage of very different types, fever and local symptoms such as inflammation and necroses can occur. Usually, the blood picture is changed. NF-κB strongly induces, for example, the serum amyloid A precursor protein in the liver in the course of induction of acute-phase proteins.

For example, the NF-κB-mediated gene expression of the interleukin-2-(II-2) gene can be inhibited.

Interleukin-2 is a cytokine which plays a central role in various inflammatory processes, inter alia, as a hematopoietic growth factor (Annu. Rev. Immunol. 12 141 (1994)). The promoter of the interleukin-2 gene is NF-κB dependent. An inhibitor of NF-κB stimulation thus opens up the possibility of preventing overshooting of II-2 production and thus of treating inflammatory processes.

In the case of other syndromes such as tissue damage after reperfusion or cirrhosis of the liver, inhibitors of NF-κB-mediated gene expression can likewise represent an important therapeutic advance. There is evidence that NF-κB-controlled genes are induced as a result of oxidation reactions which lead to oxidative stress after reperfusion of ischemic tissue. In this way, an overexpression of cytokines and cell adhesion molecules in the ischemic tissue causes excessive recruitment of infiltrating lymphocytes. The recruited lymphocytes contribute causally to the tissue damage.

The involvement of NF-κB-controlled gene expression is evident in a number of neurodegenerative disorders. In particular in the case of nervous diseases in which the redox state of cells of the neuronal tissue is disturbed, a therapeutic benefit is ascribed to the selective inhibition of genes having an NF-κB binding sequence. A disturbed redox state of neuronal cells is assumed in the case of amyotropic lateral sclerosis and in Down's syndrome.

It is known that NF-κB is a frequently encountered transcription factor in neuronal tissue and that NF-κB is a redox potential-controlled transcription factor in the brain (P. A. Bauerle, T. Henkel, Annu. Rev. Immunol. 12, 141–179, 1994). A formulation of the genes which are induced by NF-κB is shown in Table 1.

TABLE 1

Genes which are induced by NF-κB (P.A. Bauerle, T. Henkel, Annu. Rev. Immunol. 12 141–179, 1994)

| | |
|---|---|
| Immunoreceptors | Immunoglobulin κ light chain |
| | T cell receptor β |
| | T cell receptor α chain (human) |
| | Major histocompatibility complex class I (H-2K) |
| | $β_2$-microglobulin |
| | Invariant chain I |
| | Tissue factor-1 |
| Cell adhesion molecules | Endothelial leukocyte adhesion molecule 1 (ELAM-1) |
| | Vascular cell adhesion molecule 1 (VCAM-1) |
| | Intercellular cell adhesion molecule 1 (ICAM-1)* |
| Cytokines and growth factors | β-Interferon |
| | Granulocyte/macrophage colony-stimulating factor (GM-CSF) |
| | Granulocyte colony-stimulating factor (G-CSF) |
| | Macrophage colony-stimulating actor (M-CSF) |
| | Melanoma growth stimulating activity (groα-γ/MGSA) |
| | Interleukin-2 |
| | Interleukin-6 |
| | Interleukin-8 |
| | TNFα |
| | Lymphotoxin (TNF-β) |
| | Proenkephalin |
| | MPC-1/JE* |
| Acute-phase proteins | Angiotensinogen |
| | Serum amyloid A precursor |
| | Complement factor B |
| | Complement factor c4 |
| | Urokinase-type plasminogen activator* |

*The binding of NF-κB to the promoter of the gene mentioned has still not been conclusively demonstrated experimentally.

In addition to the already mentioned genes, whose activity is controlled by the release of NF-κB and which particularly play a role in inflammatory processes, septic shock and transplant rejection, NF-κB-controlled genes in viruses may also be mentioned and those which produce oncogenic cellular changes (oncogenes such as c-myc, c-rel, melanoma growth stimulating activity MGSA). In these genes too, selective inhibition of NF-κB binding is a promising, therapeutically utilizable concept. The gene expression of lymphotrophic viruses such as HIV, HTLV and Epstein-Barr virus is activated either directly or by NF-κB or NF-κB is induced in the infected host cell, which is favourable to virus replication. In addition, HIV has an NF-κB-positive action on gene expression in the cytomegalovirus (CMV) and adenovirus. Antiviral effects with NF-κB inhibitors are conceivable here too.

The preparation and the use of the substances according to the invention are evident from the following examples.

PREPARATION EXAMPLES

Example I-1

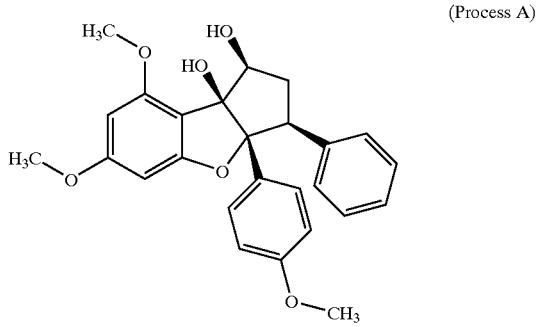
(Process A)

A solution of 1.83 g (6.5 mmol) of diiodoethane in 7 ml of THF is added to 1.92 g (12.8 mmol) of samarium and the mixture is stirred for 30 min. After a further 2 h in an ultrasonic bath, 25 ml of benzene are added and the mixture is stirred for a further 2 h. A solution of 1.40 g (3.24 mmol) of (S*,R*)-2,3-dihydro-4,6-diethoxy-2-(4-methoxyphenyl)-3-oxo-β-phenyl-2-benzofuranpropanal (rac.). (e.g. from Example II-1) in 45 ml of benzene is then added, and the mixture is additionally stirred for 3 h in an ultrasonic bath and then for a further 12 h at room temperature. After addition of 30 ml of 1 N HCl, it is extracted with ether, dried over MgSO$_4$ and concentrated. Chromatography using t-butyl methyl ether:toluene:cyclohexane=2:1:1 yields 533 mg (1.23 mmol, 38%) of racemic (1α,3aα,8bα)-3,3a-dihydro-6,8-dimethoxy-3a-(4-methoxyphenyl)-3-phenyl-1H-cyclopenta[b]benzofuran-1,8b(2H)-diol.

$^1$H-NMR (CDCl$_3$): δ (ppm) 2.38 (ddd, 1H), 2.51 (s, 1H), 2.63 (m, 1H), 3.08 (d, 1H), 3.46 (dd, 1H), 3.72 (s, 3H), 3.84 (s, 3H), 3.86 (s, 3H), 4.80 (dt, 1H), 6.10 (d, 1H), 6.27 (d, 1H), 6.69 (d, 2H), 6.98–7.12 (m, 5H), 7.20 (d, 2H).

Example I-2

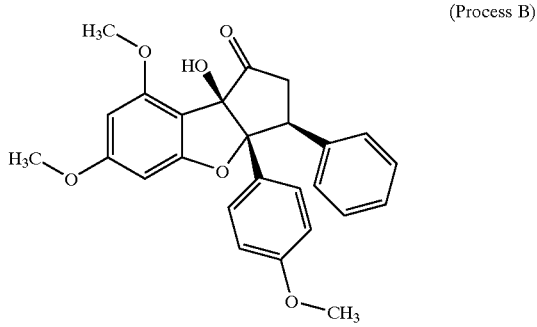
(Process B)

66 μl (0.92 mmol) of DMSO are added at −78° C. to a solution of 74 μl (0.86 mmol) of oxalyl chloride in 2.5 ml of THF. After approximately 5 min, a solution of the diol from Example I-1 (250 mg, 0.576 mmol) in 8 ml of THF is added and the mixture is stirred at −78° C. for a further 30 min. 1.19 ml (8.6 mmol) of triethylamine are then added and the mixture is stirred at −78° C. for 1 h and then at room temperature overnight. It is hydrolyzed using 15 ml of 1 N HCl and extracted with dichloromethane. After drying over MgSO$_4$, it is chromatographed using t-butyl methyl ether:cyclohexane:toluene=2:1:1. Yield 193 mg (0.446 mmol, 77%) of racemic (3α,3aα,8bα)-2,3,3a,8b-tetrahydro-8b-hydroxy-6,8-dimethoxy-3a-(4-methoxyphenyl)-3-phenyl-cyclopenta[b]benzofuran-1-one.

$^1$H-NMR (CDCl$_3$): δ (ppm) 2.94–3.10 (m, 2H), 3.10 (s, 1H), 3.70 (s, 3H), 3.83 (s, 3H), 3.85 (s, 3H), 3.89 (dd, 1H), 6.10 (d, 1H), 6.34 (d, 1H), 6.68 (d, 2H), 6.92–6.98 (m, 4H), 7.08–7.13 (m, 3H).

Example I-3

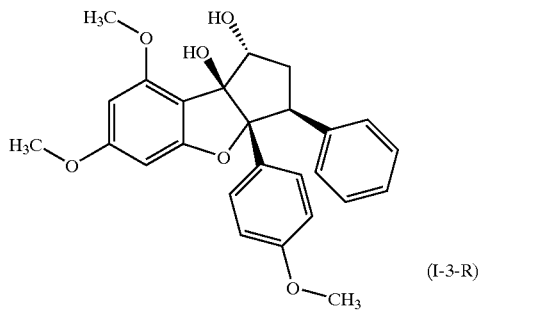
(Process C)

(I-3-R)

304 mg (1.16 mmol) of tetramethylammonium trisacetoxyborohydride are treated with 1.2 ml of acetic acid in 1.2 ml of acetonitrile. After 30 min, 100 mg (0.231 mmol) of the ketone from Example I-2 in 2.0 ml of acetonitrile is added at room temperature. The mixture is stirred overnight, cautiously hydrolyzed with 25 ml of satd. NaHCO$_3$ and extracted with dichloromethane. After drying over MgSO$_4$, it is concentrated and the residue is chromatographed using t-butyl methyl ether:cyclohexane:toluene=2:1:1. Yield: 100 mg (0.23 mmol, 100%) of racemic (1α,3β,3aβ, 8bβ)-3,3a-dihydro-6,8-dimethoxy-3a-(4-methoxyphenyl)-3-phenyl-1H-cyclopenta[b]benzofuran-1,8b(2H)-diol.

$^1$H-NMR (CDCl$_3$): δ (ppm) 2.20 (dd, 1H, J=13.6, 6.6), 2.36 (s, 1H), 2.75 (td, 1H, J=13.8, 6.4), 3.29 (s, 1H), 3.71 (s, 3H), 3.84 (s, 3H), 3.91 (s, 3H), 4.01 (dd, 1H, J=14.0, 6.5), 4.82 (d, 1H, J=6.3), 6.15 (d, 1H, J=1.9), 6.29 (s, 1H, J=1.9), 6.68 (d, 2H, J=8.9), 6.98–7.19 (m, 7H).

The direct liquid-chromatographic separation of this racemate was carried out using a chiral stationary polyamide-silica gel phase having a particle size of 10 mm based on the selector poly-(N-methacryloyl-L-leucine-d-menthylamide) and the mobile phase of n-heptane and THF (2/1; vol/vol). Such phases have been described in EP-A 0 379 917 and Angew. Chem. 103, 1685–1687 (1991). On a 500×30 mm column, it was possible to separate 200 mg per run almost quantitatively at a flow of 25 ml/min. The isomer having the [1R-(1α,3β,3aβ,8bβ)] configuration shown above, designated here as compound (I-3-R), was eluted as the second substance, the isomer (I-3-S) having the mirror image (S,R, S,R) configuration was eluted as the first substance. The optical rotation [α]$_D$ of enantiomer (I-3-R) found agrees well with that of the already known of the natural substance: [α]$_D$=−131.4 (c=0.4 CHCl$_3$)

Example I-4

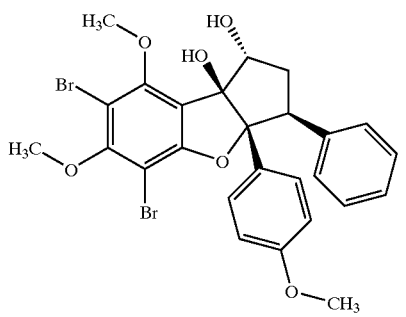

(Process D)

100 mg (0.23 mmol) of the diol from Example I-3 are introduced into 5 ml of dichloromethane and treated in portions with 112 mg (0.47 mmol) of bromine-pyridine complex. After 1 h, ether is added, and the mixture is washed with water, dried over MgSO$_4$ and concentrated. Yield 97 mg (0.15 mmol, 63%) of racemic (1α,3β,3aβ,8bβ)-5,7-dibromo-3,3a-dihydro-6,8-dimethoxy-3a-(4-methoxyphenyl)-3-phenyl-1H-cyclopenta[b]benzofuran-1,8b(2H)-diol.

$^1$H-NMR (CDCl$_3$): δ (ppm) 2.23 (dd, 1H), 2.81 (td, 1H), 3.46 (s, 1H), 3.72 (s, 3H), 3.95 (s, 3H), 4.02 (s, 3H), 4.84 (d, 1H), 6.71 (d, 2H), 7.01–7.19 (m, 7H).

Example I-5

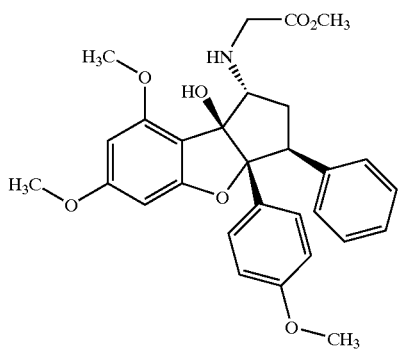

(Process E)

100 mg (0.23 mmol) of the ketone from Example 1–2 are dissolved in 6 ml of dichloromethane and stirred at room temperature for 3 h with 29 mg (0.23 mmol) of glycine methyl ester hydrochloride and 250 mg of molecular sieve 4 A. 85 mg (0.32 mmol) of tetramethylammonium trisacetoxyborohydride are then added and the mixture is stirred overnight. After filtration, NaH$_2$PO$_4$/Na$_2$HPO$_4$ buffer is added and the mixture is extracted with dichloromethane. After drying over MgSO$_4$, the extract is purified by chromatography (t-butyl methyl ether:toluene:cyclohexane= 2:1:1). Yield: 37 mg (0.07 mmol, 32%) of methyl (1α,3β, 3aβ,8bβ)-N-(3,3a-dihydro-6,8-dimethoxy-3a-(4-methoxyphenyl)-3-phenyl-cyclopenta[b]benzofuran-8b (2H)-ol-1-yl)-2-aminoacetate.

$^1$H-NMR (CDCl$_3$): δ (ppm) 2.19 (ddd, 1H), 2.62 (td, 1H), 3.50 (AB, 2H), 3.69 (s, 3H), 3.73 (s, 3H), 3.77 (dd, 1H), 3.83 (s, 3H), 3.88 (s, 3H), 4.11 (dd, 1H), 6.11 (d, 1H), 6.24 (d, 1H), 6.64 (d, 2H), 7.04–7.27 (m, 9H).

Example I-6

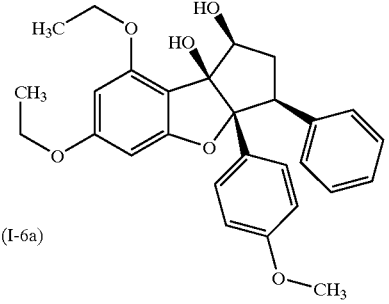

(Process A)

(I-6a)

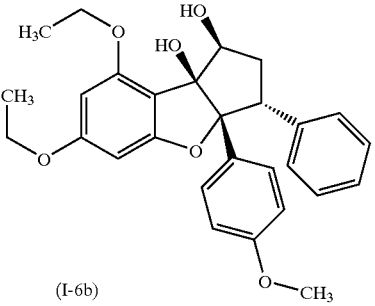

(I-6b)

Analogously to Example I-1, 1.31 g (2.85 mmol) of 2,3-dihydro-4,6-diethoxy-2-(4-methoxyphenyl)-3-oxo-β-phenyl-2-benzofuranpropanal (rac.) (e.g. from Example II-2), 1.50 g (9.96 mmol) of samarium and 2.81 g (9.96 mmol) of diiodoethane are employed. According to RP-HPLC, two isomers are obtained: 149 mg of racemic trans-isomer (1α,3β,3aα,8bα)-3,3a-dihydro-6,8-diethoxy-3a-(4-methoxyphenyl)-3-phenyl-1H-cyclopenta[b] benzofuran-1.8b(2H)-diol (I-6b):

$^1$H-NMR (CDCl$_3$): δ (ppm) 1.40 (m, 6H), 2.12 (dt 1H), 2.23 (dd, 1H), 2.39 (s, 1H), 3.81 (s, 3H), 3.99 (q, 2H), 4.04 (q, 2H), 4.26 (dd, 1H), 4.56 (d, 1H), 6.01 (d, 1H), 6.07 (d, 1H), 6.90 (d, 2H), 7.02 (m, 2H), 7.18 (m, 3H), 7.42 (d, 2H), and 37 mg of racemic cis-isomer (I-6a) of (1α,3α,3aα,8bα)-configuration: $^1$H-NMR (CDCl$_3$): δ (ppm) 1.44 (m, 6H), 2.48 (ddd, 1H), 2.62 (m, 1H), 3.47 (m, 1H), 3.71 (s, 3H), 4.07 (m, 4H), 4.80 (t, 1H), 6.09 (d, 1H), 6.23 (d, 1H), 6.70 (d, 2H), 6.99–7.12 (m, 5H), 7.19 (d, 2H).

Example I-7

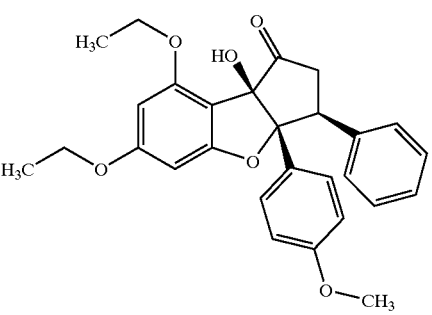

(Process B)

35 mg (0.076 mmol) of diol (I-6a) from Example I-6 are dissolved in 0.2 ml of DMSO and treated with 84 mg (0.83 mmol) of triethylamine. 122 mg (0.77 mmol) of sulfur trioxide-pyridine complex are added in 0.6 ml of DMSO and the mixture is stirred for 2 days. After addition of NaH$_2$PO$_4$/NaH$_2$PO$_4$ buffer, the mixture is extracted with dichloromethane, dried over MgSO$_4$ and concentrated. 49 mg of an oil are obtained. The mass spectrum and the product of the following reaction according to Example I-8 correlate with the structure of racemic (3α,3aα,8bα)-8b-hydroxy-6,8-diethoxy-3a-(4-methoxyphenyl)-3-phenyl-2,3,3a,8b-tetrahydrocyclopenta-[b]benzofuran-1-one.

Example I-8

(Process C)

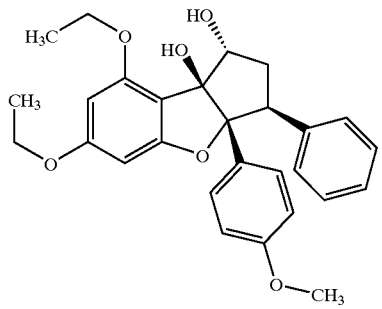

Analogously to Example I-3, 49 mg of ketone from Example 1–7 are reacted with 302 mg (1.15 mmol) of tetramethylammonium trisacetoxyborohydride. Yield: 10 mg (0.02 mmol, 29%) of racemic (1α,3 β,3aβ,8bβ)-3,3a-dihydro-6,8-diethoxy-3a-(4-methoxyphenyl)-3-phenyl-1H-cyclopenta[b]benzofuran-1,8b(2H)-diol.

$^1$H-NMR (CDCl$_3$): δ (ppm) 1.48 (m, 6H), 2.11 (dd, 1H), 2.67 (dt, 1H), 3.65 (s, 3H), 3.92 (m, 1H), 3.98 (m, 2H), 4.08 (m, 1H), 4.78 (d, 1H), 6.06 (d, 1H), 6.19 (d, 1H), 6.61 (d, 2H), 6.91–7.07 (m, 7H).

Examples I-9 I-79

The compounds of the formula (I-n) shown in Table 2 below were obtained analogously to Examples I-1 to I-8 and the general details for preparation.

TABLE 2

(I-n)

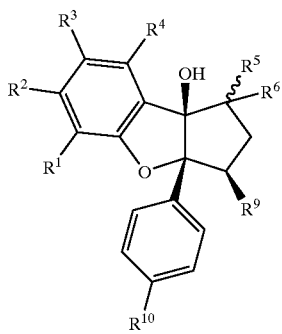

| Ex. | R$^1$ | R$^2$ | R$^3$ | R$^4$ | R$^5$ | R$^6$ | R$^9$ | R$^{10}$ | as | physical data: $^1$H-NMR (CDCl$_3$): δ[ppm] |
|---|---|---|---|---|---|---|---|---|---|---|
| I-9 | H | OCH$_3$ | H | OCH$_3$ | ◄OH (1S*)- | H | | OCH$_3$ | I-1 | 2.32(m 1H); 2.51(s 1H); 2.61(m 1H); 3.08(d 1H); 3.40(dd 1H); 3.75(s 3H); 3.84(s 3H); 3.87(s 3H); 4.80(dt 1H); 6.11(d 1H); 6.25(d 1H); 6.72(d 2H); 6.88(d 2H); 7.15–7.25(m 4H) |
| I-10 | H | OCH$_3$ | H | OCH$_3$ | ◄OH (1S*)- | H | | OCH$_3$ | I-1 | 2.23(m 1H); 2.45(dt 1H); 3.23(d 1H); 3.77(s 3H); 3.82(s 3H); 3.87(s 3H); 3.98(dd 1H); 4.89(dt 1H); 6.11(d 1H); 6.21(d 1H); 6.51(d 1H); 6.76(d 2H); 6.82(d 1H); 7.15–7.30(m 3H) |
| I-11*) | H | OCH$_3$ | H | OCH$_3$ | ◄OH (1S*)- | H | | OCH$_3$ | I-1 | 2.27(m 1H); 2.59(dt 1H); 3.09(d 1H); 3.35(dd 1H); 3.61(s 3H); 3.73(s 3H); 3.83(s 3H); 3.87(s 3H); 4.80(dt 1H); 5.36(s 1H); 6.10(d 1H); 6.23(d 1H); 6.32(d 1H); 6.54(d 1H); 6.67(d 1H); 6.74(d 2H); 7.23(d 2H). |

TABLE 2-continued (I-n)

| Ex. | R¹ | R² | R³ | R⁴ | R⁵ | R⁶ | R⁹ | R¹⁰ | as | physical data: ¹H-NMR (CDCl₃): δ[ppm] |
|---|---|---|---|---|---|---|---|---|---|---|
| I-12 | H | OCH₃ | H | OCH₃ | ◁OH (1S*)- | H | 2-(CF₃)phenyl | OCH₃ | I-1 | 2.20(ddd 1H); 2.53(ddd 1H); 3.79(s 3H); 3.81(s 3H); 3.88(s 3H); 4.92(dd 1H); 6.09(d 1H); 6.15(d 2H); 6.48(d 1H); 6.82(d 2H); 7.02(d 1H); 7.13(dd 1H); 7.35(d 2H); 7.53(d 1H) |
| I-13 | H | OCH₃ | H | OCH₃ | ◁OH (1S*)- | H | 3-(CF₃)phenyl | OCH₃ | I-1 | 2.38(ddd 1H); 2.63(ddd 1H); 3.65(m 1H); 3.85–3.92(m 9H); 4.85(dd 1H); 6.12(d 2H); 6.28(d 1H); 6.70(d 1H); 6.98(d 2H); 7.2–7.4(m 3H) |
| I-14 | H | OCH₃ | H | OCH₃ | ◁OH (1S*)- | H | 2-thienyl | OCH₃ | I-1 | 2.32(dt 1H); 2.51(s 1H); 2.73(m 1H); 3.09(d 1H); 3.62(dd 1H); 3.75(s 3H); 3.83(s 3H); 3.86(s 3H); 4.83(dt 1H); 6.10(d 1H); 6.26(d 1H); 6.63(d 1H); 6.76(m 3H); 7.00(d 1H); 7.33(d 2H) |
| I-15 | H | OCH₃ | H | OCH₃ | ◁OH (1S*)- | H | 2-furyl | OCH₃ | I-1 | 2.32(ddd 1H); 2.63(ddd 1H); 3.55(dd 1H); 3.73(s 3H); 3.82(s 3H); 3.84(s 3H); 4.75(dt 1H); 5.90(s 1H); 6.08(d 1H); 6.11(d 1H); 6.28(d 2H); 6.78(d 2H); 7.12(d 1H); 7.32(d 2H) |
| I-16 | H | OCH₃ | H | OCH₃ | ◁OH (1S*)- | H | 3-pyridyl | OCH₃ | I-1 | 2.32(ddd 1H); 2.61(ddd 1H); 3.42(dd 1H); 3.70(s 3H); 3.85(s 3H); 3.88(s 3H); 4.83(dd 1H); 6.11(d 1H); 6.25(d 1H); 6.72(d 2H); 6.96(d 1H); 7.17(m 1H); 7.20(d 2H); 8.28(m 2H) |
| I-17 | H | OCH₃ | H | OCH₃ | ◁OH (1S*)- | H | 4-pyridyl | OCH₃ | I-1 | 2.11(ddd 1H); 2.27(ddd 1H); 3.75(m 1H); 3.79(s 3H); 3.81(s 3H); 3.83(s 3H); 4.28(dd 1H); 6.04(s 2H); 6.93(d 2H); 7.05(d 2H); 7.38(d 2H); 8.51(d 2H) |
| I-18 | H | OCH₃ | H | OCH₃ | =O | | 4-Br-phenyl | OCH₃ | I-2 | 2.92(dd 1H); 3.04(dd 1H); 3.09(s 1H); 3.73(s 3H); 3.82(s 3H); 3.85(s 3H); 3.80–3.90(m 1H); 6.10(d 1H) 6.33(d 1H); 6.71(d 2H); 6.83(d 2H); 6.96(d 2H); 7.23(d 2H) |
| I-19 | H | OCH₃ | H | OCH₃ | =O | | 2,4-Cl₂-phenyl | OCH₃ | I-2 | 2.72(dd 1H); 3.02(dd 1H); 3.22(s 1H); 3.76(s 3H); 3.84(s 6H); 4.48(dd 1H); 6.11(d 1H); 6.29(d 1H); 6.33(d 1H); 6.73(d 2H); 6.82(d 1H); 7.02(d 2H); 7.33(s 1H) |
| I-20 | H | OCH₃ | H | OCH₃ | =O | | 3-OCH₃-4-OH-phenyl | OCH₃ | I-2 | 2.88(m 1H); 3.05(m 1H); 3.61(s 3H); 3.73(s 3H); 3.79(m 1H); 3.83(s 3H); 3.86(s 3H); 6.10(m 1H); 6.32(m 1H); 6.70(m 3H); 6.99(m 2H); 7.17(m 2H) |

TABLE 2-continued (I-n)

| Ex. | R¹ | R² | R³ | R⁴ | R⁵ | R⁶ | R⁹ | R¹⁰ | as | physical data: ¹H-NMR (CDCl₃): δ[ppm] |
|---|---|---|---|---|---|---|---|---|---|---|
| I-21 | H | OCH₃ | H | OCH₃ | =O | | 2-(CF₃)phenyl | OCH₃ | I-2 | 2.69(dd 1H); 3.16(dd 1H); 3.73(s 3H); 3.83(s 3H); 3.85(s 3H); 4.39(dd 1H); 6.08(d 1H); 6.21(d 1H); 6.59(d 1H); 6.72(d 2H); 7.10(d 2H); 7.11(dd 1H); 7.58(d 1H) |
| I-22 | H | OCH₃ | H | OCH₃ | =O | | 3-(CF₃)phenyl | OCH₃ | I-2 | 3.1(dq 2H); 3.71(s 3H); 3.83(s 3H); 3.88(s 3H); 6.12(d 1H); 6.37(d 1H); 6.69(d 2H); 6.93(d 2H); 7.08(d 1H); 7.12(d 1H); 7.21(d 1H); 7.35(d 1H) |
| I-23 | H | OCH₃ | H | OCH₃ | =O | | 2-thienyl | OCH₃ | I-2 | 3.16(m 2H); 3.74(s 3H); 3.79(m 1H); 3.82(s 3H); 3.85(s 3H); 3.89(dd 1H); 6.10(d 1H); 6.34(d 1H); 6.63–7.09(m 7H) |
| I-24 | H | OCH₃ | H | OCH₃ | =O | | 2-furyl | OCH₃ | I-2 | 2.60(dd 1H); 3.05(dd 1H); 3.28(s 6H); 3.38(s 3H); 4.33(d 1H); 5.90(d 1H); 6.13(dd 2H); 6.24(d 1H); 6.89(d, 2H); 7.16(d 1H); 7.60(d 2H) |
| I-25 | H | OCH₃ | H | OCH₃ | =O | | 3-pyridyl | OCH₃ | I-2 | 3.00(dq 2H); 3.72(s 3H); 3.83(s 3H); 3.85(s 3H); 3.88(s 1H); 6.12(d 1H); 6.33(d 1H); 6.70(d 2H); 6.95(d 2H); 7.00(dd 1H); 7.11(dd 1H); 8.28(d 1H); 8.33(d 1H) |
| I-26 | H | OCH₃ | H | OCH₃ | =O | | 4-pyridyl | OCH₃ | I-2 | 2.75(dd 1H); 3.28(dd 1H); 3.78(s 3H); 3.80(s 3H); 3.83(s 3H); 4.01(dd 1H); 6.03(d 1H); 6.13(sd 1H); 6.91(d 2H); 7.05(dd 2H); 7.29(d 2H); 8.45(m 2H) |
| I-27 | H | OCH₃ | H | OCH₃ | —OH (1R*)- | H | 4-bromophenyl | OCH₃ | I-3 | 2.18(dd 1H); 2.70(dt 1H); 3.28(s 1H); 3.73(s 3H); 3.86(s 3H); 3.91(s 3H); 3.94(dd 1H); 4.80(d 1H); 6.16(d 1H); 6.28(s 1H); 6.71(d 2H); 6.86(d 2H); 7.11(d 2H); 7.22(d 2H) |
| I-28 | H | OCH₃ | H | OCH₃ | —OH (1R*)- | H | 2,4-dichlorophenyl | OCH₃ | I-3 | 1.98(ddd 1H); 2.55(dt 1H); 3.77(s 3H); 3.83(s 3H); 3.93(s 3H); 4.40(dd 1H); 4.93(d 1H); 6.16(d 1H); 6.24(s 1H); 6.39(d 1H); 6.75(d 2H); 6.85(d 2H); 7.17(d 2H); 7.28(d 1H) |
| I-29 | H | OCH₃ | H | OCH₃ | —OH (1R*)- | H | 2-(CF₃)phenyl | OCH₃ | I-3 | 2.04(ddd 1H); 2.52(ddd 1H); 3.78(s 3H); 3.82(s 3H); 3.93(s 3H); 4.92(dd 1H); 4.97(dd 1H); 6.18(d 2H); 6.42(d 1H); 6.78(d 2H); 7.04(d 1H); 7.23(d 2H); 7.57(d 1H) |

TABLE 2-continued

(I-n)

| Ex. | $R^1$ | $R^2$ | $R^3$ | $R^4$ | $R^5$ | $R^6$ | $R^9$ | $R^{10}$ | as | physical data: $^1$H-NMR (CDCl$_3$): δ[ppm] |
|---|---|---|---|---|---|---|---|---|---|---|
| I-30 | H | OCH$_3$ | H | OCH$_3$ | —OH (1R*)- | H | 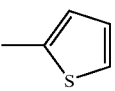 | OCH$_3$ | I-3 | 2.08(ddd 1H); 2.72(ddd 1H); 3.71(s 3H); 3.86(s 3H); 3.92(s 3H); 4.00(dd 1H); 4.85(d 1H); 6.17(d 1H); 6.30(d 1H); 6.69(d 2H); 7.10(d 2H); 7.18(m 3H); 7.32(d 1H) |
| I-31 | H | OCH$_3$ | H | OCH$_3$ | —OH (1R*)- | H | 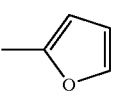 | OCH$_3$ | I-3 | 2.28(m 1H); 2.69(dt 1H); 3.43(s 1H); 3.75(s 3H); 3.84(s 3H); 3.91(s 3H); 4.02(dd 1H); 4.82(d 1H); 6.15(d 1H); 6.29(s 1H); 6.61–7.25(m 7H) |
| I-32 | H | OCH$_3$ | H | OCH$_3$ | —OH (1R*)- | H | 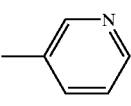 | OCH$_3$ | I-3 | 2.21(ddd 1H); 2.62(ddd 1H); 3.73(s 3H); 3.82(s 3H); 3.88(s 3H); 3.95(dd 1H); 4.88(dd 1H); 5.91(d 1H); 6.11(d 1H); 6.14(d 1H); 6.29(d 1H); 6.73(d 2H); 7.15(d 1H); 7.18(d 2H) |
| I-33 | H | OCH$_3$ | H | OCH$_3$ | —OH (1R*)- | H | 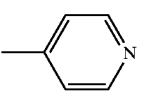 | OCH$_3$ | I-3 | 2.20(ddd 1H); 2.74(ddd 1H); 3.72(s 3H); 3.85(s 3H); 3.92(s 3H); 3.99(dd 1H); 4.85(d 1H); 6.17(d 1H); 6.30(d 1H); 6.71(d 2H); 7.03(m 1H); 7.13(d 2H); 7.17(m 1H); 8.30(d 1H); 8.33(d 1H) |
| I-34 | H | OCH$_3$ | H | OCH$_3$ | —OH (1R*)- | H | 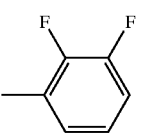 | OCH$_3$ | I-3 | 2.10(ddd 1H); 2.33(ddd 1H); 3.71(dd 1H); 3.78(s 3H); 3.82(s 3H); 3.84(s 3H); 4.68(ddd 1H); 6.09(d 1H); 6.12(d 1H); 6.88(m 1H); 6.91(d 2H); 7.31(d 2H); 8.39(d 2H) |
| I-35 | H | OCH$_3$ | H | OCH$_3$ | —OH (1R*) | H | 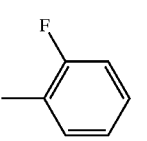 | OCH$_3$ | I-3 | 2.11(m 1H); 2.72(m 1H); 3.79(s 3H); 3.84(s 3H); 3.90(s 3H); 3.95(m 1H); 4.97(m 1H); 6.15(d 1H); 2.29(d 1H); 2.29(d 1H); 6.46(m 1H); 6.65–7.85(m 3H); 7.18(d 2H) |
| I-36 | H | OCH$_3$ | H | OCH$_3$ | —OH (1R*) | H | 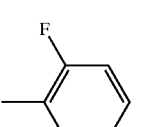 | OCH$_3$ | I-3 | 2.12(ddd 1H); 2.73(ddd 1H); 3.73(s 3H); 3.84(s 3H); 3.90(s 3H); 4.25(dd 1H); 4.88(dd 1H); 6.12(d 1H); 6.30(d 2H); 6.69(d 2H); 6.72–6.90(m 3H); 7.05(m 1H); 7.16(d 2H) |
| I-37 | H | OCH$_3$ | H | OCH$_3$ | —OH (1R*) | H | 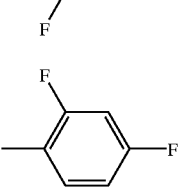 | OCH$_3$ | I-3 | 2.09(ddd 1H); 2.69(ddd 1H); 3.74(s 3H); 3.83(s 3H); 3.90(s 3H); 4.18(dd 1H); 4.88(dd 1H); 6.13(d 1H); 6.28(d 1H); 6.5–6.7(m 3H); 6.72(d 2H); 7.17(d 2H) |
| I-38 | H | OCH$_3$ | H | OCH$_3$ | —OH (1R*) | H |  | OCH$_3$ | I-3 | 2.09(ddd 1H); 3.05(ddd 1H); 3.73(s 3H); 3.83(s 3H); 3.91(s 3H); 4.24(dd 1H); 4.92(dd 1H); 6.13(d 1H); 6.28(d 1H); 6.63(dd 2H); 6.72(d 2H); 7.10(m 1H); 7.30(d 2H) |

TABLE 2-continued

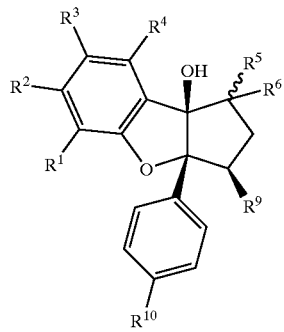

(I-n)

| Ex. | R¹ | R² | R³ | R⁴ | R⁵ | R⁶ | R⁹ | R¹⁰ | as | physical data: ¹H-NMR (CDCl₃): δ[ppm] |
|---|---|---|---|---|---|---|---|---|---|---|
| I-39 | H | OCH₃ | H | OCH₃ | —OH (1R*) | H | 4-methoxyphenyl | OCH₃ | I-3 | 2.15(ddd 1H); 2.69(ddd 1H); 3.71(s 3H); 3.72(s 3H); 3.84(s 3H); 3.90(s 3H); 4.21(dd 1H); 4.31(dd 1H); 6.13(d 1H); 6.28(d 1H); 6.64(d 2H); 6.70(d 2H); 6.88(d 2H); 7.13(d 2H) |
| I-40 | H | OCH₃ | H | OCH₃ | —OH (1R*) | H | 4-fluorophenyl | OCH₃ | I-3 | 2.12(ddd 1H); 2.72(ddd 1H); 3.72(s 3H); 3.84(s 3H); 3.90(s 3H); 4.23(dd 1H); 4.88(dd 1H); 6.12(d 1H); 6.29(d 1H); 6.69(d 2H); 6.72–6.88(m 3H); 7.04(m 1H); 7.16(d 2H) |
| I-41 | H | OCH₃ | H | OCH₃ | —OH (1R*) | H | 3-fluorophenyl | OCH₃ | I-3 | 2.20(ddd 1H); 2.70(ddd 1H); 3.72(s 3H); 3.85(s 3H); 3.90(s 3H); 3.98(dd 1H); 4.80(dd 1H); 6.15(d 1H); 6.30(d 1H); 6.70(d 2H); 6.72–6.8(m 3H); 7.07(m 1H); 7.12(d 2H) |
| I-42 | H | OCH₃ | H | OCH₃ | —OH (1R*) | H | phenyl | F | I-3 | 2.18(dd 1H); 2.71(ddd 1H); 3.23(s 6H); 3.90(s 3H); 4.00(dd 1H); 4.82(d 1H); 6.14(d 2H); 6.30(d 2H); 6.82(m 2H); 6.96(m 2H); 7.10(m 2H); 7.18(m 3H) |
| I-43 | H | OCH₃ | H | OCH₃ | —OH (1R*) | H | 2-methoxy-4-acetylphenyl | OCH₃ | I-3 | 2.05(m 1H); 2.32(m 1H); 2.37(s 3H); 3.66(s 3H); 3.78(s 3H); 3.80(s 3H); 3.83(s 3H); 4.21(dd 1H); 4.67(dd 1H); 6.08(d 1H); 6.16(d 1H); 6.72(d 2H); 6.90(d 2H); 7.0–7.5(m 3H) |
| I-44 | H | OCH₃ | H | OCH₃ | —OH (1R*) | H | 5-bromothiophen-2-yl | OCH₃ | I-3 | 2.20(ddd 1H); 2.62(ddd 1H); 3.78(s 3H); 3.83(s 3H); 3.90(s 3H); 4.0(dd 1H); 4.80(dd 1H); 6.13(d 1H); 6.28(d 1H); 6.35(m 1H); 6.71(d 1H); 6.80(d 2H); 7.25(m 2H) |
| I-45 | H | OCH₃ | H | OCH₃ | —OH (1R*) | H | 5-methylthiophen-2-yl | OCH₃ | I-3 | 2.30(s 3H); 2.49(ddd 1H); 2.85(ddd 1H); 3.60(m 1H); 3.75(s 3H); 3.82(s 6H); 5.19(dd 1H); 6.09(d 1H); 6.23(d 1H); 6.35–6.52(m 3H); 6.79(d 2H); 7.23(d 2H) |
| I-46 | H | OCH₃ | H | OCH₃ | —OH (1R*) | H | benzo[1,3]dioxol-5-yl | OCH₃ | I-3 | 2.15(m 1H); 2.65(m 1H); 3.72(s 3H); 3.84(s 3H); 3.90(s 3H); 3.89(m 1H); 4.78(m 1H); 6.13(d 1H); 6.28(d 1H); 6.47(m 1H); 6.58(d 2H); 6.72(d 2H); 7.16(d 2H) |
| I-47 | H | OCH₃ | H | OCH₃ | —OH (1R) | H | biphenyl-4-yl | OCH₃ | I-3 | 2.23(m 1H); 2.78(ddd 1H); 3.71(s 3H); 3.86(s 3H); 3.91(s 3H); 4.03(dd 1H); 4.83(dd 1H); 6.15(d 1H); 6.31(d 1H); 6.70(d 2H); 7.06(d 2H); 7.18(d 2H); 7.28–7.42(m 5H); 7.52(d 2H) |

TABLE 2-continued

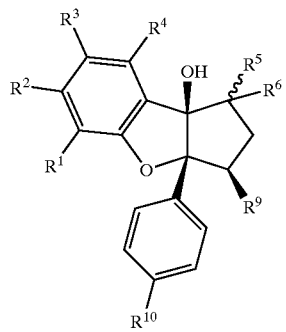

(I-n)

| Ex. | R¹ | R² | R³ | R⁴ | R⁵ | R⁶ | R⁹ | R¹⁰ | as | physical data: ¹H-NMR (CDCl₃): δ[ppm] |
|---|---|---|---|---|---|---|---|---|---|---|
| I-48 | H | OCH₃ | H | OCH₃ | —OH (1R) | H | 3-phenoxyphenyl | OCH₃ | I-3 | 2.18(m 1H); 2.70(ddd 1H); 3.73(s 3H); 3.82(s 3H); 3.90(s 3H); 4.01(dd 1H); 4.79(m 1H); 6.12(d 1H); 6.27(d 1H); 6.68–6.78(m 6H); 6.88(d 1H); 7.04(m 1H); 7.10–7.17(m 3H); 7.23–7.30(m 2H) |
| I-49 | H | OCH₃ | H | OCH₃ | —OH (1R) | H | 3-fluorophenyl | F | I-3 | 2.20(m 1H); 2.70(m 1H); 3.25(s 3H); 3.92(s 3H); 4.00(dd 1H); 4.81(dd 1H); 6.18(d 1H); 6.31(d 1H); 6.70–6.90(m 5H); 7.06(m 1H); 7.20(m 2H) |
| I-50 | H | OCH₃ | H | OCH₃ | =O | | 2,3-difluorophenyl | OCH₃ | I-2 | 2.91(dd 1H); 3.02(dd 1H); 3.7–3.9(m 10H); 6.11(d 1H); 6.33(d 1H); 6.71(d 2H); 6.90(m 2H); 7.02(d 2H); 7.31(d 1H) |
| I-51 | H | OCH₃ | H | OCH₃ | =O | | 2-fluorophenyl | OCH₃ | I-2 | 2.94(dd 1H); 3.02(dd 1H); 3.72(s 3H); 3.83(s 3H); 3.85(s 3H); 4.22(m 1H); 6.10(d 1H); 6.32(d 1H); 6.58(dt 1H); 6.70(d 2H); 6.81(dt 1H); 6.91(dt 1H); 7.01(d 2H); 7.08(m 1H) |
| I-52 | H | OCH₃ | H | OCH₃ | =O | | 2,6-difluorophenyl | OCH₃ | I-2 | 2.88(dd 1H); 3.01(dd 1H); 3.75(s 3H); 3.83(s 3H); 3.85(s 3H); 4.18(dd 1H); 6.10(d 1H); 6.31(d 1H); 6.52(m 2H); 6.67(dt 1H); 6.73(d 2H); 7.01(d 2H) |
| I-53 | H | OCH₃ | H | OCH₃ | =O | | 2,4-difluorophenyl | OCH₃ | I-2 | 2.98(dd 1H); 3.32(dd 1H); 3.74(s 3H); 3.82(s 3H); 3.84(s 3H); 4.30(t 3H); 6.09(d 1H); 6.31(d 1H); 6.64(t 1H); 6.69(d 2H); 6.97(m 1H); 7.06(m 1H); 7.12(d 2H) |
| I-54 | H | OCH₃ | H | OCH₃ | =O | | 4-methoxyphenyl | OCH₃ | I-2 | 2.91(dd 1H); 3.03(dd 1H); 3.72(s 3H); 3.73(s 3H); 3.83(s 3H); 3.85(s 3H); 4.22(t 1H); 6.10(d 1H); 6.33(d 1H); 6.65(d 2H); 6.72(d 2H); 6.84(d 2H); 6.97(d 2H) |
| I-55 | H | OCH₃ | H | OCH₃ | =O | | 3-fluorophenyl | OCH₃ | I-2 | 2.94(dd 1H); 3.05(dd 1H); 3.72(s 3H); 3.83(s 3H); 3.85(s 3H); 3.88(m 1H); 6.11(d 1H); 6.35(d 1H); 6.70(d 2H); 6.72(m 2H); 6.69(dt 1H); 6.97(d 2H); 7.07(m 1H) |

TABLE 2-continued

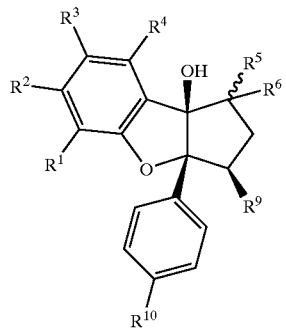

(I-n)

| Ex. | R¹ | R² | R³ | R⁴ | R⁵ | R⁶ | R⁹ | R¹⁰ | as | physical data: ¹H-NMR (CDCl₃): δ[ppm] |
|---|---|---|---|---|---|---|---|---|---|---|
| I-56 | H | OCH₃ | H | OCH₃ | =O | | 4-F-phenyl | OCH₃ | I-2 | 2.94(dd 1H); 3.02(dd 1H); 3.73(s 3H); 3.83(s 3H); 3.84(s 3H); 4.24(dd 1H); 6.10(d 1H); 6.32(d 1H); 6.59(dt 1H); 6.70(d 2H); 6.79(dt 1H); 6.90(m 1H); 7.02(d 2H); 7.08(m 1H) |
| I-57 | H | OCH₃ | H | OCH₃ | =O | | phenyl | F | I-2 | 2.98(dd 1H); 3.07(dd 1H); 3.83(s 3H); 3.86(s 3H); 3.90(m 1H); 6.12(d 1H); 6.35(d 1H); 6.83(t 2H); 6.93(m 2H); 7.01(m 2H); 7.12(m 3H) |
| I-58 | H | OCH₃ | H | OCH₃ | =O | | 2-OCH₃-4-C(O)CH₃-phenyl | OCH₃ | I-2 | 2.37(2 3H); 2.72(m 1H); 3.22(dd 1H); 3.66(s 3H); 3.76(s 3H); 3.78(s 3H); 3.80(s 3H); 3.95(d 1H); 6.01(d 1H); 6.15(d 1H); 6.50–6.7(m 3H); 6.79(d 2H); 6.90(d 2H) |
| I-59 | H | OCH₃ | H | OCH₃ | =O | | 5-Br-thien-2-yl | OCH₃ | I-2 | 2.85(dd 1H); 3.11(dd 1H); 3.77(s 3H); 3.81(s 3H); 3.84(s 3H); 3.98(dd 1H); 6.10(d 1H); 6.32(d 1H); 6.36(dd 1H); 6.71(d 1H); 6.79(d 2H); 7.08(d 2H) |
| I-60 | H | OCH₃ | H | OCH₃ | =O | | 5-CH₃-thien-2-yl | OCH₃ | I-2 | 2.30(s 3H); 2.68(dd 1H); 3.53(dd 1H); 3.77(s 3H); 3.82(s 3H); 3.85(s 3H); 4.79(t 1H); 6.09(d 1H); 6.25(d 1H); 6.39(AB 2H); 6.79(d 2H); 7.35(d 2H) |
| I-61 | H | OCH₃ | H | OCH₃ | =O | | benzo[1,3]dioxol-5-yl | OCH₃ | I-2 | 2.89(dd 1H); 3.02(dd 1H); 3.74(s 3H); 3.82(s 3H); 3.85(t 1H); 3.85(s 3H); 5.86(AB 2H); 6.10(d 1H); 6.33(d 1H); 6.40(dd 1H); 6.48(bs 1H); 6.57(dd 1H); 6.72(d 2H); 7.00(d 2H) |
| I-62 | H | OCH₃ | H | OCH₃ | =O | | biphenyl-4-yl | OCH₃ | I-2 | 3.01(dd 1H); 3.09(dd 1H); 3.71(s 3H); 3.84(s 3H); 3.86(s 3H); 3.94(dd 1H); 6.12(d 1H); 6.36(d 1H); 6.70(d 2H); 7.00(d 2H); 7.01(d 2H); 7.33(t 1H); 7.37(d 2H); 7.40(t 2H); 7.51(d 2H) |
| I-63 | H | OCH₃ | H | OCH₃ | =O | | 3-phenoxyphenyl | OCH₃ | I-2 | 2.93(dd 1H); 3.03(dd 1H); 3.73(s 3H); 3.82(s 3H); 3.84(s 3H); 3.88(t 1H); 6.10(d 1H); 6.31(d 1H); 6.63(bs 1H); 6.72(d 2 + 1H); 6.77(dd 1H); 6.81(d 1H); 6.98(d 2H); 7.09(m 1H); 7.12(t 1H); 7.17(m 1H); 7.30(m 2H) |
| I-64 | H | OCH₃ | H | OCH₃ | =O | | 3-F-phenyl | F | I-2 | 2.94(dd 1H); 3.07(dd 1H); 3.83(s 3H); 3.86(s 3H); 3.90(m 1H); 6.12(d 1H); 6.35(d 1H); 6.70(m 2H); 6.80(dd 1H); 6.86(tt 2H); 7.00–7.10(m 3H) |

TABLE 2-continued

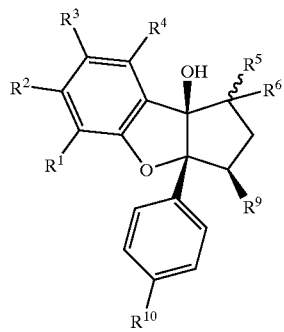

(I-n)

| Ex. | R¹ | R² | R³ | R⁴ | R⁵ | R⁶ | R⁹ | R¹⁰ | as | physical data: ¹H-NMR (CDCl₃): δ[ppm] |
|---|---|---|---|---|---|---|---|---|---|---|
| I-65 | H | OCH₃ | H | OCH₃ | ◁OH | H | 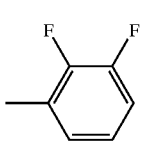 | OCH₃ | I-1 | |
| I-66 | H | OCH₃ | H | OCH₃ | ◁OH | H | 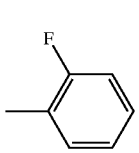 | OCH₃ | I-1 | 2.39(dt 1H); 2.48(td 1H); 3.73(s 3H); 3.83(s 3H); 3.86(s 3H); 4.22(t 1H); 4.84(t 1H); 6.10(d 1H); 6.25(d 1H); 6.72(m 2 + 1H); 6.78(dt 1H); 6.86(m 1H); 7.03(m 1H); 7.26(d 2H) |
| I-67 | H | OCH₃ | H | OCH₃ | ◁OH | H | 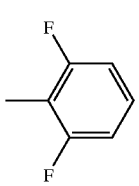 | OCH₃ | I-1 | 2.33(dt 1H); 2.46(td 1H); 3.75(s 3H); 3.82(s 3H); 3.86(s 3H); 3.8–3.9(m 1H); 4.84(dt 1H); 6.09(d 1H); 6.23(d 1H); 6.52(dt 1H); 6.61(m 1H); 6.68(m 1H); 6.74(d 2H); 7.25(d 2H) |
| I-68 | H | OCH₃ | H | OCH₃ | ◁OH | H | 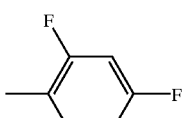 | | I-1 | 2.50(td 1H); 2.82(m 1H); 3.76(s 3H); 3.82(s 3H); 3.87(s 3H); 3.92(t 1H); 4.78(dt 1H); 6.10(d 1H); 6.22(d 1H); 6.63(t 1H); 6.75(d 2H); 6.95(m 1H); 7.02(m 1H); 7.35(d 2H) |
| I-69 | H | OCH₃ | H | OCH₃ | ◁OH | H | 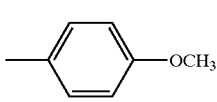 | OCH₃ | I-1 | 2.32(m 1H); 2.40(td 1H); 3.40(dd 1H); 3.71(s 3H); 3.73(s 3H); 3.83(s 3H); 3.86(s 3H); 4.79(t 1H); 6.10(d 1H); 6.25(d 1H); 6.64(d 2H); 6.72(d 2H); 6.90(d 2H); 7.21(d 2H) |
| I-70 | H | OCH₃ | H | OCH₃ | ◁OH | H | 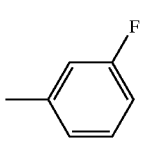 | OCH₃ | I-1 | 2.34(dt 1H); 2.63(td 1H); 3.45(dd 1H); 3.72(s 3H); 3.84(s 3H); 3.86(s 3H); 4.80(t 1H); 6.11(d 1H); 6.26(d 1H); 6.71(d 2H); 6.73–6.81(m 2H); 7.05(m 1H); 7.20(d 2H) |
| I-71 | H | OCH₃ | H | OCH₃ | ◁OH | H | 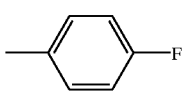 | OCH₃ | I-1 | 2.36(m 1H); 2.62(m 1H); 3.46(dd 1H); 3.83(s 3H); 3.86(s 6H); 4.82(dd 1H); 6.12(d 1H); 6.37(d 1H); 6.83(m 2H); 6.98(m 2H); 7.05–7.12(m 3H); 7.16(m 1H); 7.24(m 1H) |

TABLE 2-continued

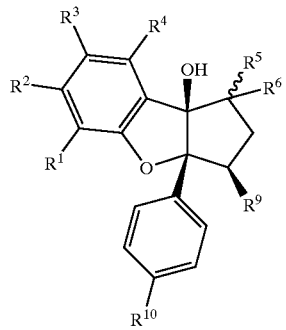

(I-n)

| Ex. | R¹ | R² | R³ | R⁴ | R⁵ | R⁶ | R⁹ | R¹⁰ | as | physical data: ¹H-NMR (CDCl₃): δ[ppm] |
|---|---|---|---|---|---|---|---|---|---|---|
| I-72 | H | OCH₃ | H | OCH₃ | ◁OH | H | 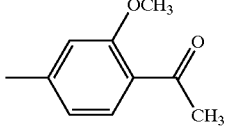 | OCH₃ | I-1 | 2.36(m 1H); 2.62(td 1H); 3.46(dd 1H); 3.83(s 3H); 3.86(s 3H); 4.83(t 1H); 6.11(d 1H); 6.26(d 1H); 6.83(t 2H); 6.97(m 2H); 7.05–7.25(m 5H) |
| I-73 | H | OCH₃ | H | OCH₃ | ◁OH | H | 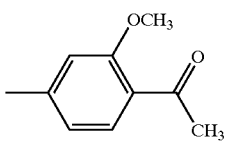 | OCH₃ | I-1 | Mixture of the diastereomers |
| I-74 | H | OCH₃ | H | OCH₃ | ◁OH | H | 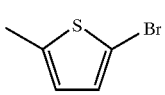 | OCH₃ | I-1 | 2.25(dt 1H); 2.68(td, 1H); 3.53(m 1H); 3.78(s 3H); 3.82(s 3H); 3.85(s 3H); 4.80(t 1H); 6.10(d 1H); 6.24(d 1H); 6.36(dd 1H); 6.69(d 1H); 6.81(d 2H); 7.34(d 2H) |
| I-75 | H | OCH₃ | H | OCH₃ | ◁OH | H | 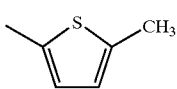 | OCH₃ | I-1 | 2.28(dt 1H); 2.30(s 3H); 2.69(td 1H); 3.53(dd 1H); 3.77(s 3H); 3.82(s 3H); 3.85(s 3H); 4.79(t 1H); 6.09(d 1H); 6.24(d 1H); 6.39(AB 2H); 6.79(d 2H); 7.34(d 2H) |
| I-76 | H | OCH₃ | H | OCH₃ | ◁OH | H | 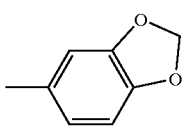 | OCH₃ | I-1 | 2.29(m 1H); 2.59(td 1H); 3.37(dd 1H); 3.74(s 3H); 3.83(s 3H); 3.86(s 3H); 4.76(dt 1H); 5.84(m 2H); 6.10(d 1H); 6.24(d 2H); 6.47(d 1H); 6.56(bs 1H); 6.57(d 1H); 6.74(d 2H); 7.22(d 2H) |
| I-77 | H | OCH₃ | H | OCH₃ | ◁OH | H | 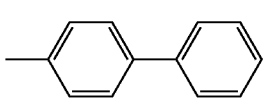 | OCH₃ | I-1 | 2.17(d 2H); 3.17(s 1H); 3.79(s 3H); 3.81(s 3H); 3.82(s 3H); 4.61(t 1H); 6.05(d 1H); 6.14(d 1H); 6.88(d 2H); 6.89(m 1H); 7.03(t 1H); 7.15(m 1H); 7.21(m 1H); 7.26(s 5H); 7.43(d 2H) |
| I-78 | H | OCH₃ | H | OCH₃ | ◁OH | H | 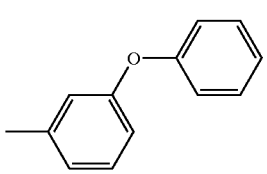 | OCH₃ | I-1 | 2.60(m 1H); 2.88(m 1H); 3.81(s 3H); 3.85(m 6H); 4.07(m 1H); 5.85(d 1H); 6.14(d 1H); 6.43(d 2H); 6.98(m 1H); 7.2–7.4(m 8H); 7.48(m 2H) |

TABLE 2-continued (I-n)

[Structure: benzofuran-fused cyclopentane with substituents R1–R10, OH, phenyl group]

| Ex. | R¹ | R² | R³ | R⁴ | R⁵ | R⁶ | R⁹ | R¹⁰ | as | physical data: ¹H-NMR (CDCl₃): δ[ppm] |
|---|---|---|---|---|---|---|---|---|---|---|
| I-79 | H | OCH₃ | H | OCH₃ | ◁OH | H | [3-fluorophenyl] | F | I-1 | 2.32(m 1H); 2.62(m 1H); 3.45(dd 1H); 3.84(s 3H); 3.86(s 3H); 4.82(dt 1H); 6.12(d 1H); 6.26(d 1H); 6.75(m 2H); 6.86(t 2H); 7.05(m 1H); 7.17(tt 1H); 7.26(m 2H) |

*⁾:The diastereomer pairs (3S*; 3R*) were first separated at this stage

Preparation of the Precursors

Example II-1

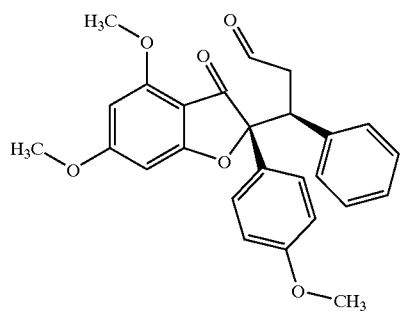
(II-1a)

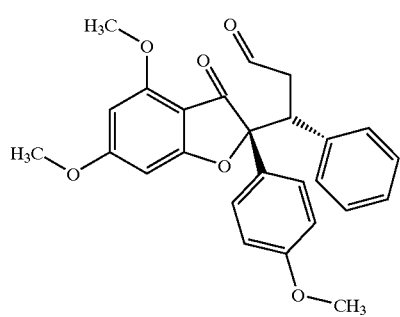
(II-1b)

5.0 g (16.5 mmol) of 4,6-dimethoxy-2-(4-methoxyphenyl)-benzofuran-3-one are introduced into 50 ml of tert-butanol and warmed to 60° C. 1.05 ml of benzyltrimethylammonium hydroxide solution (Triton® B 40% in methanol, 3.0 mmol) and 2.2 ml (17.5 mmol) of freshly distilled E-cinnamaldehyde are then added, and the mixture is stirred at 60° C. for 3 h. 50 ml of 1 N HCl are then added, and the mixture is extracted with CH₂Cl₂ (3×50 ml). After drying over MgSO₄, the extract is chromatographed (t-butyl methyl ether:toluene:cyclohexane=2:1:1). In addition to a mixed fraction of 1.03 g (2.39 mmol, 14%), 2.16 g (5,0 mmol, 30%) of racemic (S*,R*)-3-[4,6-dimethoxy-2-(4-methoxyphenyl)-3-oxo-2,3-dihydrobenzofuran-2-yl]-3-phenylpropanal (II-1a) and 635 mg (1.47 mmol, 9%) of racemic (R*,R*) derivative (II-1b) are obtained.

(II-1a): ¹H-NMR (CDCl₃): δ (ppm) 2.68 (ddd, 1H), 3.03 (ddd, 1H), 3.70 (s, 3H), 3.79 (s, 3H), 3.85 (s, 3H), 4.20 (dd, 1H), 5.80 (d, 1H), 6.21 (d, 1H), 6.89 (d, 2H), 7.06–7.19 (m, 3H), 7.32 (d, 2H), 7.66 (d, 2H), 9.42 (dd, 1H).

(II-1b): ¹H-NMR (CDCl₃): δ (ppm) 2.66 (ddd, 1H), 3.00 (ddd, 1H), 3.70 (s, 3H), 3.87 (s, 3H), 3.90 (s, 3H), 4.13 (dd, 1H), 5.99 (d, 1H), 6.31 (d, 1H), 6.69 (d, 2H), 7.05–7.19 (m, 5H), 7.38 (d, 2H), 9.48 (dd, 1H).

Example II-2

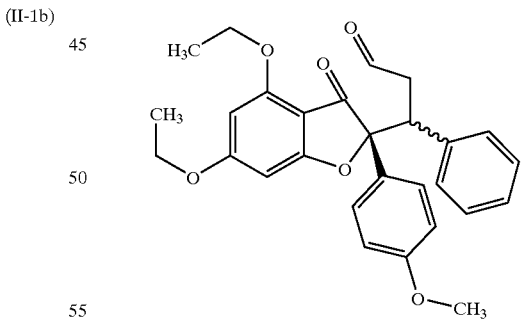

4.17 g (12.7 mmol) of 4,6-diethoxy-2-(4-methoxyphenyl) benzofuran-3-(2H)-one are introduced into 40 ml of methanol and warmed to 60° C. 137 mg (2.54 mmol) of sodium methoxide in 4 ml of methanol, 2.1 ml (16.5 mmol) of E-cinnamaldehyde and 20 ml of toluene are then added. The mixture is stirred at 60° C. overnight. 1 N HCl is then added and the mixture is extracted with dichloromethane. After drying over MgSO₄, the extract is chromatographed (t-butyl methyl ether:toluene:cyclohexane=1:1:1). 1.31 g of a mixture of diastereomers of 3-[4,6-diethoxy-2-(4- methoxyphenyl)-3-oxo-2,3-dihydrobenzofuran-2-yl]-3-phenylpropanal are obtained.

$^1$H-NMR (CDCl$_3$) selected signals: δ (ppm) 5.78 (d, 1H), 6.17 (d, 1H), 6.89 (d, 2H), 7.65 (d, 2H), 9.39 (m, 1H) and 5.98 (d, 1H), 6.28 (d, 1H), 6.68 (d, 2H), 7.38 (d, 2H), 9.48 (dd, 1H).

Examples II-3 to II-26

The compounds of the formula (II-n) listed in Table 3 below were obtained analogously to Examples II-1 and II-2 and the general details for preparation.

TABLE 3

(II-n)

| Ex. | R$^1$ | R$^2$ | R$^3$ | R$^4$ | R$^9$ | R$^{10}$ | physical data: $^1$H-NMR (CDCl$_3$): δ [ppm] |
|---|---|---|---|---|---|---|---|
| II-3a | H | OCH$_3$ | H | OCH$_3$ | 4-Br-C$_6$H$_4$ (3S*)- | OCH$_3$ | 2.68(dd 1H); 3.00(ddd 1H); 3.72(s 3H); 3.79(s 3H); 3.87(s 3H); 4.17(dd 1H); 5.84(d 1H); 6.21(d 1H); 6.88(d 2H); 7.15–7.30(m 5H); 7.62(d 2H); 9.40(d 1H) |
| II-3b | H | OCH$_3$ | H | OCH$_3$ | 4-Br-C$_6$H$_4$ (3R*)- | OCH$_3$ | 2.67(dd 1H); 2.98(ddd 1H); 3.72(s 3H); 3.88(s 3H); 3.91(s 3H); 4.12(dd 1H); 6.01(d 1H); 6.30(d 1H); 6.70(d 2H); 7.05(d 2H); 7.15–7.30(m 3H); 7.48(d 2H); 9.48(d 1H) |
| II-4a | H | OCH$_3$ | H | OCH$_3$ | 2,4-Cl$_2$-C$_6$H$_3$ (3S*)- | OCH$_3$ | 2.90(m 2H); 3.76(s 3H); 3.79(s 3H); 3.89(s 3H); 4.78(m 1H); 5.90(d 1H); 6.28(d 1H); 6.88(d 2H); 7.15–7.35(m 3H); 7.63(d 2H); 7.85(d 1H); 9.41(m 1H) |
| II-4b | H | OCH$_3$ | H | OCH$_3$ | 2,4-Cl$_2$-C$_6$H$_3$ (3R*)- | OCH$_3$ | 2.68(dd 1H); 2.84(ddd 1H); 3.72(s 3H); 3.88(s 3H); 3.91(s 3H); 4.87(dd 1H); 6.02(d 1H); 6.30(d 1H); 6.70(d 2H); 7.10–7.30(m 2H); 7.42(d 2H); 7.54(d 1H); 9.49(m 1H) |
| II-5 | H | OCH$_3$ | H | OCH$_3$ | 3-OCH$_3$-4-OH-C$_6$H$_3$ 3(S*/R*)- | OCH$_3$ | S*: 2.65(t 1H); 2.95(dd 1H); 4.12(dd 1H); 5.83(d 1H); 6.22(d 1H); 6.88(d 2H); 7.65(d 2H); 9.42(s 1H), R*: 2.60(t 1H); 2.98(dd 1H); 4.04(dd 1H); 6.01(d 1H); 6.29(d 1H); 6.70(d 2H); 7.41(d 2H); 9.51(d 1H) Signal selection; S*/R* isomer ratio: 1.7:1 |
| II-6a | H | OCH$_3$ | H | OCH$_3$ | benzo[1,3]dioxol-5-yl (3S*)- | OCH$_3$ | 2.63(dd 1H); 2.97(ddd 1H); 3.76(s 3H); 3.80(s 3H); 3.89(s 3H); 4.13(dd 1H); 5.87(m 3H); 6.25(d 1H); 6.62(d 1H); 6.82(m 2H); 6.90(d 2H); 7.65(d 2H); 9.42(m 1H) |
| II-6b | H | OCH$_3$ | H | OCH$_3$ | benzo[1,3]dioxol-5-yl (3R*)- | OCH$_3$ | 2.61(dd 1H); 2.91(ddd 1H); 3.71(s 3H); 3.89(s 3H); 3.93(s 3H); 4.09(dd 1H); 5.89(m 2H); 6.02(d 1H); 6.34(d 1H); 6.58(m 2H); 6.72(d 2H); 6.80(d 1H); 7.41(d 2H); 9.50(d 1H) |

TABLE 3-continued

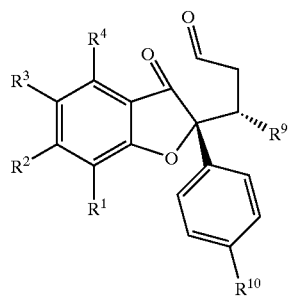

(II-n)

| Ex. | R¹ | R² | R³ | R⁴ | R⁹ | R¹⁰ | physical data: $^1$H-NMR (CDCl$_3$): δ [ppm] |
|---|---|---|---|---|---|---|---|
| II-7a | H | OCH$_3$ | H | OCH$_3$ | 2-(CF$_3$)phenyl (3S*)- | OCH$_3$ | 2.72(ddd 1H); 2.53(ddd 1H); 3.79(s 3H); 3.81(s 3H); 3.88(s 3H); 4.92(dd 1H); 6.09(d 1H); 6.15)d 1H); |
| II-8a | H | OCH$_3$ | H | OCH$_3$ | 3-(CF$_3$)phenyl (3S*)- | OCH$_3$ | 2.78(ddd 1H); 3.10(ddd 1H); 3.74(s 3H); 3.80(s 3H); 3.92(s 3H); 4.52(dd 1H); 5.92(d 1H); 6.32(d 1H); 6.88(d 2H); 7.27(m 2H); 7.53(dd 1H); 7.63(m 1H); 9.43(s 1H) |
| II-9a | H | OCH$_3$ | H | OCH$_3$ | 2-thienyl (3R*)- | OCH$_3$ | 2.64(dd 1H); 2.96(ddd 1H); 3.74(s 3H); 3.79(s 3H); 3.88(s 3H); 4.58(dd 1H); 5.87(d 1H); 6.29(d 1H); 6.78(dd 1H); 6.89(d 2H); 7.00(d 1H); 7.04(d 1H); 7.64(d 2H); 9.46(d 1H) |
| II-9b | H | OCH$_3$ | H | OCH$_3$ | 2-thienyl (3S*)- | OCH$_3$ | 2.64(dd 1H); 2.95(ddd 1H); 3.72(s 3H); 3.87(s 3H); 3.91(s 3H); 4.46(dd 1H); 6.00(d 1H); 6.33(d 1H); 6.69–7.19(m 5H); 7.45(d 2H); 9.53(d 1H) |
| II-10a | H | OCH$_3$ | H | OCH$_3$ | 2-furyl (3R*)- | OCH$_3$ | 2.60(ddd 1H); 3.04(ddd 1H); 3.78(s 6H); 3.88(s 2H); 4.32(dd 1H); 5.90(d 1H); 6.13(d 1H); 6.15(d 1H); 6.23(d 1H); 6.88(d 2H); 7.16(d 1H); 7.60(d 2H); 9.48(s 2H) |
| II-11a | H | OCH$_3$ | H | OCH$_3$ | 3-pyridyl (3S*)- | OCH$_3$ | 2.80(dd 1H); 3.10(dd 1H); 3.71(s 3H); 3.79(s 3H); 3.88(s 3H); 4.21(dd 1H); 5.83(d 1H); 6.23(d 1H); 6.90(d 2H); 7.13(dd 1H); 7.62(d 2H); 7.70(d 1H); 8.34(dd 1H); 8.57(d 1H); 9.45(s 1H) |
| II-12a | H | OCH$_3$ | H | OCH$_3$ | 4-pyridyl (3S*)- | OCH$_3$ | 2.73(dd 1H); 3.08(ddd 1H); 3.71(s 3H); 3.88(s 3H); 3.91(s 3H); 4.14(dd 1H); 6.02(d 1H); 6.30(d 1H); 6.71(d 2H); 7.13(d 2H); 7.38(d 2H); 8.37(d 2H); 9.50(d 1H) |
| II-13a | H | OCH$_3$ | H | OCH$_3$ | 2,3-difluorophenyl (3S*)- | OCH$_3$ | 2.69(ddd 1H); 3.02(ddd 1H); 3.83(s 3H); 3.79(s 3H); 3.87(s 3H); 4.21(dd 1H); 5.83(d 1H); 6.23(d 1H); 6.79(m 1H); 6.89(m 2H); 7.03(m 1H); 7.13(m 2H); 7.64(m 1H); 9.41(dd 1H) |

TABLE 3-continued

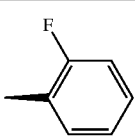

(II-n)

| Ex. | R¹ | R² | R³ | R⁴ | R⁹ | R¹⁰ | physical data: ¹H-NMR (CDCl₃): δ [ppm] |
|---|---|---|---|---|---|---|---|
| II-14a | H | OCH₃ | H | OCH₃ | 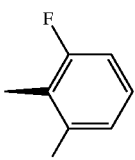<br>(3S*)- | OCH₃ | 2.79(ddd 1H); 3.03(ddd 1H); 3.72(s 3H); 3.79(s 3H); 3.87(s 3H); 4.55(dd 1H); 5.84(d 1H); 6.27(d 1H); 6.86–6.97(m 4H); 7.07–7.19(m 2H); 7.64(m 2H); 9.42(dd 1H) |
| II-15a | H | OCH₃ | H | OCH₃ | 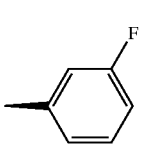<br>(3S*)- | OCH₃ | 2.78(ddd 1H); 3.01(ddd 1H); 3.75(s 3H); 3.78(s 3H); 3.87(s 3H); 4.50(dd 1H); 5.88(d 1H); 6.26(d 1H); 6.67(m 2H); 6.88(d 2H); 7.26(m 1H); 7.64(d 2H); 9.43(dd 1H) |
| II-16a | H | OCH₃ | H | OCH₃ | 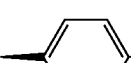<br>(3S*)- | OCH₃ | 2.33(m 1H); 2.63(m 1H); 3.45(dd 1H); 3.72(s 3H); 3.83(s 3H); 3.89(s 3H); 4.81(dd 1H); 6.11(d 1H); 6.27(d 1H); 6.70–6.81(m 2H); 6.93–6.99(m 4H); 7.18–7.22(m 2H); 9.41(dd 1H) |
| II-17a | H | OCH₃ | H | OCH₃ | 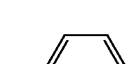<br>(3S*)- | OCH₃ | 2.40(dd 1H); 3.02(ddd 1H); 3.72(s 3H); 3.79(s 3H); 3.88(s 3H); 4.55(dd 1H); 5.85(d 1H); 6.26(d 1H); 6.89(d 2H); 6.92(m 1H); 7.09(m 1H); 7.18(m 1H); 7.28(m 1H); 7.66(d 2H); 9.42(m 1H) |
| II-18a | H | OCH₃ | H | CH₃ | 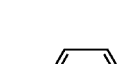<br>(3S*)- | OCH₃ | 2.63(dd 1H); 2.99(ddd 1H); 3.69(s 3H); 3.71(s 3H); 3.79(s 3H); 3.88(s 3H); 4.16(dd 1H); 5.81(d 1H); 6.21(d 1H); 6.68(d 2H); 6.88(d 2H); 7.23(d 2H); 7.64(d 2H); 9.38(m 1H) |
| II-19a | H | OCH₃ | H | OCH₃ | <br>(3S*)- | F | 2.63(dd 1H); 3.08(ddd 1H); 3.71(s 3H); 3.88(s 3H); 4.20(dd 1H); 5.31(d 1H); 6.22(d 1H); 7.05–7.18(m 7H); 7.30(d 2H); 9.41(m 1H) |
| II-20a | H | OCH₃ | H | OCH₃ | 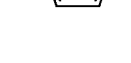<br>(3R*)- | OCH₃ | 2.62(ddd 1H); 2.91(ddd 1H); 3.77(s 3H); 3.78(s 3H); 3.90(s 3H); 4.49(dd 1H); 5.91(d 1H); 6.30(d 1H); 6.74(m 2H); 6.88(d 2H); 7.60(d 2H); 9.48(m 1H) |
| II-21a | H | OCH₃ | H | OCH₃ | (3R*)- | OCH₃ | 2.30(s 3H); 2.58(m 1H); 2.90(ddd 1H); 3.76(s 3H); 3.76(s 3H); 3.79(s 3H); 3.98(s 3H); 4.44(dd 1H); 5.88(d 1H); 6.29(d 1H); 6.41(m 1H); 6.73(d 1H); 6.88(d 2H); 7.62(d 2H); 9.46(m 1H) |

TABLE 3-continued

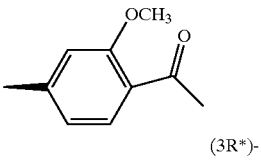

(II-n)

| Ex. | R¹ | R² | R³ | R⁴ | R⁹ | R¹⁰ | physical data: ¹H-NMR (CDCl₃): δ [ppm] |
|---|---|---|---|---|---|---|---|
| II-22a | H | OCH₃ | H | OCH₃ | 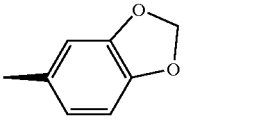 (3R*)- | OCH₃ | 2.37(s 3H); 2.61(m 1H); 2.98(ddd 1H); 3.70(s 3H); 3.72(s 3H); 3.88(s 3H); 3.90(s 3H); 4.04(dd 1H); 6.00(d 1H); 6.29(d 1H); 6.72(d 2H); 7.12–7.20(m 3H); 7.40(d 2H); 9.78(dd 1H) |
| II-23a | H | OCH₃ | H | OCH₃ | 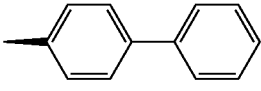 | OCH₃ | 2.61(m 1H); 2.94(ddd 1H); 3.74(s 3H); 3.79(s 3H); 3.88(s 3H); 4.12(dd 1H); 5.84(m 2H); 6.22(d 1H); 6.60(d 1H); 6.91(m 2H); 6.89(d 2H); 7.63(d 2H); 9.40(m 1H) |
| II-24a | H | OCH₃ | H | OCH₃ | 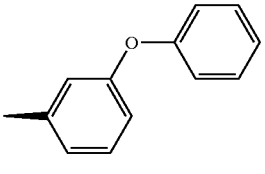 | OCH₃ | 2.71(ddd 1H); 3.07(ddd 1H); 3.70(s 3H); 3.80(s 3H); 3.85(s 3H); 4.25(dd 1H); 5.80(d 1H); 6.23(d 1H); 6.90(d 2H); 7.13(m 1H); 7.35–7.42(m 6H); 7.50(d 2H); 7.68(d 2H); 9.42(dd 1H) |
| II-25a | H | OCH₃ | H | OCH₃ | 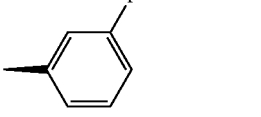 | OCH₃ | 2.66(ddd 1H); 2.99(ddd 1H); 3.76(s 6H); 3.79(s 3H); 4.20(dd 1H); 5.86(d 1H); 6.12(d 1H); 6.68(dd 2H); 6.76(m 1H); 6.88(d 2H); 7.05(m 1H); 7.13–7.20(m 3H); 7.22(m 1H), 7.63(d 2H); 9.41(m 1H) |
| II-26a | H | OCH₃ | H | OCH₃ | 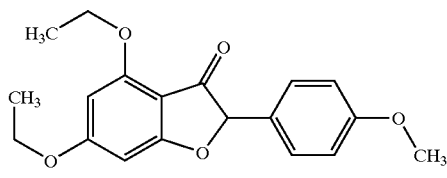 | F | 2.63(ddd 1H); 3.03(ddd 1H); 3.72(s 3H); 3.88(s 3H); 4.20(dd 1H); 5.83(d 1H); 6.23(d 1H); 6.80(m 1H); 7.00–7.20(m 5H); 7.72(m 2H); 9.42(m 1H) |

Example IV-1

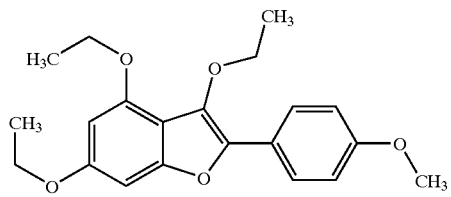

15.62 g of 3,4,6-triethoxy-2-(4-methoxyphenyl)benzofuran (e.g. from Example IV-1') are introduced into 200 ml of methanol, treated with 200 ml of 0.5 N HCl and heated under reflux for 3 h. After cooling the solution, the precipitate is filtered off with suction. Yield: 12.69 g of 4,6-diethoxy-2-(4-methoxyphenyl)benzofuran-3-(2H)-one.

¹H-NMR (CDCl₃): δ (ppm) 1.43 (m, 6H), 3.79 (s, 3H), 4.13 (m, 4H), 5.41 (s, 1H), 6.02 (d, 1H), 6.19 (d, 1H), 6.89 (d, 2H), 7.31 (d, 2H).

Example IV-1'

10 g (36.7 mmol) of 4,6-dihydroxy-2-(4-methoxyphenyl)benzofuran-3-(2H)-one are dissolved in 400 ml of acetone and treated with 32.5 g (6.4 mmol) of potassium carbonate. 36.3 g (6.4 mmol) of diethyl sulphate are added and the mixture is heated under reflux for 2.5 h. 50 ml of methanol are then added, and the mixture is heated under reflux for a further hour, filtered off and concentrated. The crude product is chromatographed on silica gel (ethyl acetate:cyclohexane=1:3). Yield: 15.62 g of 3,4,6-triethoxy-2-(4-methoxyphenyl)benzofuran.

¹H-NMR (CDCl₃): δ (ppm) 1.43 (m, 9H), 3.85 (s, 3H), 4.06 (q, 2H), 4.14 (q, 2H), 4.21 (q, 2H), 6.29 (d, 1H), 6.58 (d, 1H), 6.96 (d, 2H), 7.92 (d, 2H).

Example V-1

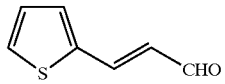

5 g of NaOH are dissolved in 60 ml of water and 30 ml of ethanol are added. 22.5 g (239 mmol) of thiophene-2-carbaldehyde are added dropwise in the course of 15 min and 50 g (1.135 mol) of an acetaldehyde solution (40% in water) are slowly added dropwise (1.5 h at 0° C.). The mixture is stirred at 0° C. for 1 h, neutralized with ice-cold acetic acid, extracted with dichloromethane, and the extract is washed with water, dried over MgSO₄, carefully concentrated and distilled at 1 mbar/80–95° C. Yield: 8.74 g (26% of theory) of E-3-(2-thienyl)-propenal.

¹H-NMR (CDCl₃): δ (ppm) 6.52 (dd, 1H), 7.11 (dd, 1H), 7.37 (d, 1H), 7.51 (d, 1H), 7.59 (d, 1H), 9.63 (d, 1H).

Example V-2

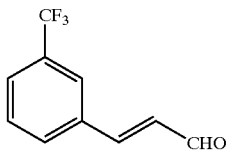

1) 12.29 ml of 1M diisobutylaluminum hydride solution in THF diluted with 20 ml of THF are introduced under argon and a solution of 1.00 g (4.095 mmol) of ethyl E-3-trifluoromethylcinnamate in 20 ml of THF is added dropwise. The mixture is subsequently stirred for 30 min, hydrolyzed with water, then extracted with dichloromethane, and the combined extracts are dried and concentrated. Column chromatography on silica gel (mobile phase:cyclohexane:ethylacetate:=7:3) yields in the first fraction 420 mg (50.7% of theory) of E-3-trifluoromethylcinnamyl alcohol which is employed further for the oxidation.

¹H-NMR (CDCl₃): δ (ppm) 1.68 (s, 1H); 4.38 (d, 2H); 6.43 (dt, 1H); 6.66 (d, 1H); 7.42 (dd, 1H); 7.49 (d, 1H); 7.53 (d, 1H); 7.62 (s, 1H).

2) At −70° C., 395.5 mg (3.324 mmol) of oxalyl chloride are introduced in 2 ml of THF under argon, 259.3 mg (3.324 mmol) of dimetyl sulphoxide are added dropwise and the mixture is subsequently stirred for 5 min. A solution of the 420 mg (2.077 mmol) of alcohol from the first stage in 5 ml of THF are added dropwise to this at at most −70° C. and the mixture is subsequently stirred for 30 min. After dropwise addition of 3.147 g (31.16 mmol) of triethylamine at −70° C., the mixture is first stirred at this temperature for 1 h, then subsequently stirred at room temperature for 16 h. It is hydrolyzed using phosphate buffer, then extracted with dichloromethane, and the combined extracts are dried and concentrated. Column chromatography on silica gel (mobile phase:cyclohexane:ethyl acetate=8:2) yields in the first fraction 180 mg (43.3% of theory) of E-3-trifluoromethylcinnamaldehyde.

¹H-NMR (CDCl₃): δ (ppm) 6.78 (dd, 1H); 7.53 (dd, 1H); 7.57 (d, 1H); 7.70 (d, 1H); 7.78 (d, 1H); 9.75 (d, 1H).

USE EXAMPLES

Example A

Inhibition of the NF-κB-Mediated Gene Expression of the Tumour Necrosis Factor-α (TNFα) Gene in Human Monocytes The promoter of the human TNFα gene contains 3 NF-κB binding sequences which are designated as k1, k2 and k3. The NF-κB binding sequences are found in the promoter of the TNFα gene in the nucleotide positions k1=−587 to −577, k2=−210 to −202 and k3=−98 to −87 and these DNA sequences specifically bind NF-κB (A. E. Goldfield et al., Proc. Natl. Acad. Sci. USA 87, 9769–9773, 1990). Lipopolysaccharide or phorbol esters (such as phorbol myristate acetate) induce NF-κB release (M. J. Lenardo et al., Cell 58, 227–229, 1989).

The following biological test is therefore carried out to detect the inhibition of the NF-κB-mediated TNFα gene expression by the substances described here.

Mononuclear cells from donor blood are isolated using Vacutainer CPT™ tubes (Becton Dickinson and Company, Franklin Lakes, N.J. 07417-1885), according to the instructions of the manufacturer. The Vacutainer CPT tubes contain 1.0 ml of phosphate-buffered saline with 120 USP units of sodium heparin above 3.0 g of a polyester gel which is covered with a layer of 2.0 ml of a Ficoll solution. After the centrifugation of the donor blood, the monocytes are taken from a zone above the polyester gel and inoculated at a cell density of 250×10⁵ cells per well into 96-well microtiter plates for cell culture.

The cells are incubated for 4 to 6 hours in RPMI-1640 medium (Gibco BRL, Life Technologies GmbH, Dieselstr. 5, 76344 Eggenstein). The culture supernatant is then aspirated, RPMI-1640 medium is added again and the substances to be tested are added in concentrations customarily between 0 μM (negative control) and 20 μM. Bacterial lipopolysaccharide (LPS), Sigma-Aldrich Chemie GmbH, Grünwalder Weg 30, 82039 Deisenhofen, Order No.: L 4391, is then added in a concentration of 125 ng/ml for the stimulation of the NF-κB-mediated TNFα gene expression. After a further incubation of 18 hours at 37° C. in a 5% CO₂ atmosphere, culture supernatant is removed from the microtiter plates and the TNFα content therein is determined quantitatively using commercially available enzyme-bound immunosorbent assays (ELISA).

TNFα ELISA for concentration determination are marketed, for example, by Sigma-Aldrich Chemie GmbH, Grünwalder Weg 30, 82039 Deisenhofen under the name Human TNFα ELISA Kit, Order No.: CKH-200A. According to the use instructions of the manufacturer, the concentration of the TNFα formed in the culture supernatant of the monocyte culture is determined quantitatively after LPS stimulation with and without inhibitor substance.

The results of the TNFα-concentration determination are plotted against one another in an x/y graph. The graph of the y coordinates (TNFα concentration in the culture supernatant) and of the x coordinates (concentration of the inhibitor employed) enables the inhibition of the NF-κB-mediated TNFα synthesis to be read off as a function of the concentration of the inhibitor substance. In this way, it is possible to read off from the graph that active compound concentration of the added inhibitor which inhibits, for example, TNFα synthesis by 50%. This active compound concentration which produces a 50% inhibition is called the effective inhibitor concentration for 50% inhibition (IC₅₀).

In this case, for example, the following compounds showed that they are potent inhibitors of NF-κB-mediated TNFα synthesis:

| Active compound from Preparation Example No. | IC$_{50}$ |
|---|---|
| I-1 | 0.5 |
| I-3-R | 0.1 |
| I-5 | 0.5 |

Example B
Inhibition of the NF-κB-Mediated Gene Expression of the Human Tissue Factor Gene in Monocytes Tissue factor is a membrane protein which is the primary initiator of the blood coagulation cascade and takes on a key function in cardiovascular diseases such as unstable angina pectoris, acute implications after plaque rupture, vascular occlusions of varying etiology, arteriosclerotic processes and other illnesses such as septic shock or cancer. The tissue factor gene is induced by NF-κB activation, in particular in monocytes and endothelial cells. The promoter of the human tissue factor gene contains an NF-κB binding site which contributes crucially to the activation of the promoter (P. Oeth et al. Arteriosclerosis, Thrombosis, and Vascular Biology 17, 365–374, 1997).

Therefore, for the further detection of the inhibition of the NFκB-mediated gene expression by the inhibitors according to the invention, the following biological test was carried out:

The promoter fragment of the human tissue factor gene which contains the NF-κB binding sequence was cloned with oligonucleotide primers of the sequence 5'-TCC CTC GAG ATC TCC CAG AGG CAA ACT GCC AGA T-3' (5' primer of position −925) and 5'-TCC TCG AGC CAT GGC TAC CAG TTG GGC GGC GAG ATC-3' (3' primer containing the ATG start codon of the coding sequence of the tissue factor gene) by means of the polymerase chain reaction (PCR) and fused by means of an NcoI/XhoI cloning with the luciferase start codon in the plasmid pGL3-basic vector (Promega Corp. 2800 Woods Hollow Road, Madison, Wis. 53711-5399 USA). By means of this, the expression of the luciferase in the recombinant plasmid thus resulting is regulated by the human tissue factor promoter. This expression construct was subjected to DNA sequencing analysis and transfected into the monocyte cell line RAW 264.7 (American Type Culture Collection 12301 Parklane Drive, Rockville, Md. 20852, USA). The transfection, selection and clone analysis was carried out by standard methods, such as have been described (see Transfection of Mammalian Cells in Culture, L. G. Davis et al. Basic Methods in Molecular Biology, Elsevier Sci. Publishing Co., New York 1986). After the selection of RAW 8 clones which had integrated the expression construct stably in the genome, one of these transfectants, called RAW-A3, was selected for the testing of the inhibitors.

Test Procedure:

106 RAW-A3 cells are inoculated into each depression in 12-well microtiter plates. The serum concentration is lowered stepwise in the course of three days in the RPMI medium from 10% fetal calf serum to 0.5% and 0.1% serum content in order to lower the serum-dependent tissue factor promoter activation to a minimum. After culture in medium containing 0.1% serum for 24 hours, the NF-κB inhibitor is added and serum is then added up to a concentration of 15% in the medium for promoter induction.

After a further 6 hours, the culture supernatant is aspirated and the cells are processed for the measurement of the luciferase activity according to the procedure of the "Luciferase Assay System" (Technical Bulletin of Promega, 2800 Woods Hollow Road, Madison, Wis. 53711-5399 USA, Products E4030, E1483, E1501). The cell lyzate is incubated with the luciferase assay substrate and measured in a luminometer to measure the emitted light. In a plot in an x/y graph with the light emitted in each case (indicated in relative light units) as y coordinates and the inhibitor concentrations as x coordinates, a graph for f(x) results in which the half-maximal y value of an inhibitor concentration x is to be assigned which corresponds to the inhibitor concentration IC$_{50}$ in this test.

For example, the IC$_{50}$-value of the compound according to Preparation Example I-1 is 20 μM and 1–52 μM. The NF-κB-mediated expression of the luciferase by the inhibitors according to the invention with a concentration in the lower micromolar or in the submicromolar range points to the high activity of the inhibition of an NF-κB-mediated gene expression.

Example C
Inhibition of the NF-κB-Mediated Gene Expression of the Tumour Necrosis Factor-α (TNFα) Gene in Human Monocytes as a Function of Three Different TNFα Synthesis Stimuli The NF-κB-mediated induction of TNFα-synthesis is independent of the different stimuli which are employed by LPS, opsonized zymosan or phorbol myristate acetate (PMA) for the activation of the TNFα promoter (A. Baldwin, Annual Rev. Immunology 14, 649, 1996). Therefore the use of the inhibitors according to the invention should also lead to a comparatively strong inhibition of TNFα synthesis independently of the nature of the stimulation of the TNFα synthesis.

The tests for this detection of the stimulus-independent inhibition of TNFα synthesis were carried out by the type of test procedure exactly as is described in Example A with the difference that in addition to LPS as a stimulus, cell culture batches were also stimulated with 100 nM PMA or with 100 μg/ml of opsonized zymosan. Zymosan and phorbol myristate acetate (PMA) can be ordered from Sigma, Gr ünwalder Weg 30, 82041 Deisenhofen, Germany under Order Nos Z4250 and P8139. Zymosan is opsonized in human serum.

Independently of the stimulus, the NF-κB-inhibitors according to the invention inhibit the TNFα synthesis in human monocytes as was shown in Example A in a comparative manner with IC$_{50}$ values in the submicromolar range. Thus for the compound according to Preparation Example I-1 the IC$_{50}$ value after PMA stimulus is 0.10 μM and for compound I-5 0.09 μM.

Example D
Inhibition of the NF-κB-Mediated Gene Expression of the Adhesion Protein ELAM-1 to Human Umbilical Cord Endothelial Cells (HUVEC)

The recruitment of leukocytes from the blood circulation into the extravascular space is essential in inflammatory responses and in the repair of tissue damage. The process of leukocyte infiltration comprises a number of steps connected in series. The initial interaction between leukocytes and the endothelium of the blood vessels is mediated by TNF and II-1-dependent expression of the adhesion protein ELAM-1 on the endothelium. It mediates the so-called rolling of the leukocytes along the blood vessel wall. The transcriptional regulation of the ELAM-1 expression is dependent both on the nuclear factor-κB (NF-κB) activation and binding to the ELAM-1 promoter and on the "AP-1 binding site [M A. Read et., Biol. chem. Vol. 272, 2753–2761, (1997)].

The influence of compound I-3-R on the expression of ELAM-1 was checked in two different test batches. In one functional batch, the adhesion of human neutrophils to TNF-α-stimulated HUVEC cells was measured. The expression of ELAM-1 on the surface of the HUVECs was determined using a fluorescence-labeled ELAM-1-specific monoclonal antibody by means of FACS (cell sorting) analysis.

Experimental Procedure: ELAM-Dependent Neutrophil Adhesion to Endothial Cells

The neutrophils were isolated from human blood (100 ml). To this end, 3.5 ml of Polyprep was introduced into a centrifuge bucket and carefully coated with 5 ml of blood. After centrifuging at 2100 min$^{-1}$ for 30 minutes, the neutrophil band in the center of the centrifuge bucket was aspirated. After 1:2 dilutions in Clonetics endothelial cell basal medium (EBM), the neutrophils were again centrifuged at 1000 min$^{-1}$ for 20 minutes and then made up to a cell concentration of 10$^6$ cells/ml.

The umbilical cord endothelial cells were grown to confluence in EBM+10% FCS in 96 well microtiter plates. At the start of the experiment, the medium was replaced by EBM without FCS and the experimental substances then employed. After 20 minutes, the HUVECs were stimulated using 10 nM TNF-α. After incubation for 4 hours replacement was carried out by 200 μl/well of the neutrophil suspension. The neutrophils had been labeled with a 25 μM BCECP fluorescent dye solution for 20 minutes beforehand. After incubation for 30 minutes, the BCECP neutrophil solution was stripped off with excess neutrophils and replaced by 200 μl/well of 0.5% strength NaOH solution. The fluorescence of the adherent neutrophils was then measured in a fluorescence photometer.

Both the adhesion of the neutrophils to TNF-α-stimulated HUVECs, and the expression of ELAM-1 on the cell surface were inhibited to 50% by the compound. The maximum inhibition of cell adhesion was determined at 50 nM for compound I-3-R. The maximum 50% inhibition of the ELAM-1 expression is in good agreement with the simultaneously NF-κB and AP-1-dependent regulation of the ELAM-1 promoter.

Experimental Procedure Quantitative Measurement of the TNF-Induced Expression of ELAM-1 in HUVECs Umbilical cord endothelial cells (HUVEC) were cultured as described above and incubated for 4 hours in the presence or absence of test substances in the presence or absence of 10 ng/ml of TNF. The cells were dissolved out of the microtiter plates by incubation with 5 mM EDTA in PBS, centrifuged at 1000 min$^{-1}$ for 5 minutes, and incubated at RT in 100 μl of PBS plus 1% bovine serum albumin (BSA, Sigma-Aldrich GmbH, Order No. A 7906) and an anti-ELAM 1 antibody (monoclonal antibody, Becton and Dickinson, Erembodegem, Belgium, Order No. 550023, 30 μg/ml). After 15 minutes, the cells were again centrifuged, the supernatant was discarded and the cells were washed in PBS plus 1% BSA. After centrifugation again, the cell pellet obtained was incubated for a duration of 15 minutes in PBS plus 1% BSA and a goat-anti-mouse antibody (Dianova, Raboisen 5, Hamburg; Order No. 115-096-062; 30 μg/ml). After centrifuging and washing again, the cells were taken up in 1 ml of PBS plus 1% BSA and measured at 488 nm in a flow cytometer (Becton and Dickinson). The intensity of the fluorescence as a function of bound anti-ELAM-1 antibody per cell is measured by this process. 5000 cells were measured for each value.

After incubation with anti-ELAM-1 antibodies, HUVECs which had been stimulated with TNF for 4 hours showed markedly stronger fluorescence signals than cells which, on the other hand, had not been incubated with TNF. The compound from Preparation Example I-3-R was able to inhibit this induced expression of ELAM-1 in a concentration range between 0.05 μM and 5 μM significantly, but the expression of ELAM-1 was completely inhibited at none of the concentrations investigated.

Example E

Inhibition of Interleukin-2 Synthesis

For the testing of the inhibitory action of cyclopentabenzene derivatives on interleukin-2 synthesis, a receptor gene cell line was used which contains the interleukin-2 promoter coupled to the luciferase gene. The promoter contains the DNA sequence from −480 to +4. The vector employed is pGL3; the starting cell line in which the total construct has been stably transfected is SS-1. The culture medium for this cell line was RPMI 1640 (Gibco, Rockille). It additionally contained: 100 μg/ml of streptomycin, 100 U/ml of penicillin, 2 mM L-glutamine, 10% heat-inactivated FBS and 800 μg/ml of G418 sulfate.

Test Procedure

The reporter gene test cell line was inoculated into 96-well plates to 1×10$^6$ cells per well in Phenol Red-free RPMI with the additives and incubated at 37° C. in an atmosphere of 5% $CO_2$, 95% air with phorbol 12-myristate 13-acetate (PMA; 5 ng/ml) and ionomycin (10 M; 0.4 μg/ml) for 24 hours. The test substances were added simultaneously with PMA.

Measurement of the Luciferase Activity:

For the generation of the luminescence, LucLite™ solution (Packard, Meriden, Conn.) was added to a concentration of 100 μl/well and the luminescence was measured in a luminometer (Luminoskan, Labsystems) immediately after addition.

The compound from Preparation Example I-3-R was able to inhibit the induction of the luciferase activity to 50% ($IC_{50}$) at a concentration of 5 to 10 nM.

What is claimed is:

1. A compound of the formula (I)

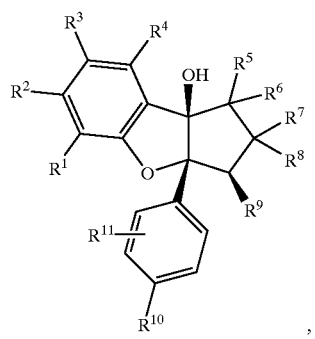

in which

R¹ and R³ independently of one another in each case represent hydrogen, halogen or alkyl, R² and R⁴ independently of one another in each case represent halogen, alkyl or alkoxy optionally substituted by fluorine and chlorine, R⁵ represents hydroxyl, alkylamino or the radical —NR¹²—CHR¹³—COOR¹⁴, in which R¹² represents hydrogen or alkyl, R¹³ represents one of the radicals of a natural amino acid or represents hydrogen. (C₁–C₄)-alkyl optionally substituted by amino or hydroxyl or represents mercaptomethyl, methylthioethyl, carboxymethyl, carboxyethyl, carbamoylmethyl, carbamoylethyl, guanidinopropyl or represents phenyl or benzyl optionally substituted by amino, nitro, halogen, hydroxyl or methoxy or represents naphthylmethyl, indolylmethyl, imidazolylmethyl, triazolylmethyl or pyridylmethyl, where functional groups can optionally be present in protected form, or R¹² and R¹³ together represent —(CH₂)₃— and —(CH₂)₄—, and R¹⁴ represents alkyl, benzyl or another C-terminal protective group, R⁶ represents hydrogen or R⁵ and R⁶ together represent oxygen (oxo), R⁷ and R⁸ in each case represent hydrogen, R⁹ represents phenyl or hetaryl, which in each case can optionally be substituted up to four times by substituents of the group: halogen, C₁–C₆-alkyl, hydroxyl, C₁–C₄-alkoxy, C₁–C₄-alkylthio, C₁–C₄-alkylcarbonyl, phenyl, phenoxy, hetaryl, hetaryloxy, C₁–C₄-alkyl substituted by fluorine or chlorine, C₁–C₄-alkoxy substituted by fluorine or chlorine, C₁–C₄-alkylthio substituted by fluorine or chlorine, C₁–C₄-alkylcarbonyl substituted by fluorine or chlorine, R¹⁰ represents hydrogen, halogen, alkyl or alkoxy and R¹¹ represents hydrogen, halogen or alkyl, or a pharmaceutically acceptable salt thereof, with the exception of 3,3a-dihydro-6,8-dimethoxy-3a-(4-methoxyphenyl)-3-phenyl-1H-cyclopenta[b]benzofuran-1,8b(2H)-diol and 2,3,3a,8b-tetrahydro-8b-hydroxy-6,8-dimethoxy-3a-(4-methoxyphenyl)-3-phenyl(-1H-cyclopenta[b)benzofuran-1-one.

2. The compound of claim 1 in which

R¹ and R³ independently of one another in each case represent hydrogen, fluorine, chlorine, bromine or C₁–C₆-alkyl, R² and R⁴ independently of one another in each case represent fluorine, chlorine, bromine, C₁–C₆-alkyl or C₁–C₄-alkoxy optionally substituted by fluorine or chlorine, R⁵ represents hydroxyl, C₁–C₄-alkylamino or the radical —NR¹²—CHR¹³—COOR¹⁴, R⁶ represents hydrogen or R⁵ and R⁶ also together represent oxygen (oxo), R⁷ and R⁸ in each case represent hydrogen, R⁹ represents phenyl, methylenedioxyphenyl or 5- or 6-membered hetaryl having 1 or 2 heteroatoms from the series consisting of nitrogen, oxygen and sulphur which in each case can optionally be substituted up to four times by substituents of the group: halogen, C₁–C₆-alkyl, hydroxyl, C₁–C₄-alkoxy, C₁–C₄-alkylthio, C₁–C₄-alkylcarbonyl, phenyl, phenoxy, hetaryl, hetaryloxy, C₁–C₄-alkyl substituted by fluorine or chlorine, C₁–C₄-alkoxy substituted by fluorine or chlorine, C₁–C₄-alkylthio substituted by fluorine or chlorine, C₁–C₄-alkylcarbonyl substituted by fluorine or chlorine, R¹⁰ represents hydrogen, fluorine, chlorine, C₁–C₆-alkyl or C₁–C₆-alkoxy, R¹¹ represents hydrogen, fluorine, chlorine, bromine or C₁–C₆-alkyl, R¹² represents hydrogen or C₁–C₄-alkyl, R¹³ represents hydrogen, (C₁–C₄)-alkyl optionally substituted by amino or hydroxyl or represents mercaptomethyl, methylthioethyl, carboxymethyl, carboxyethyl, carbamoylmethyl, carbamoylethyl, guanidinopropyl or represents phenyl or benzyl optionally substituted by amino, nitro, halogen, hydroxyl or methoxy or represents naphthylmethyl, indolylmethyl, imidazolylmethyl, triazolylmethyl or pyridylmethyl, where functional groups can optionally be present in protected form, or $R^{12}$ and $R^{13}$ also together represent —(CH$_2$)$_3$— or —(CH$_2$)$_4$—, $R^{14}$ represents (C$_1$–C$_6$)-alkyl, benzyl or another C-terminal protective group, or a pharmaceutically acceptable salt thereof.

3. The compound of claim 1 in which $R^1$ and $R^3$ independently of one another in each case represent hydrogen, fluorine, chlorine, bromine, methyl or ethyl, $R^2$ and $R^4$ independently of one another in each case represent fluorine, chlorine, bromine, C$_1$–C$_4$-alkyl or methoxy or ethoxy optionally substituted by fluorine or chlorine, $R^5$ represents hydroxyl, C$_1$–C$_4$-alkylamino or the radical —NR$^{12}$—CHR$^{13}$—COOR$^{14}$, $R^6$ represents hydrogen, or $R^5$ and $R^6$ together represent oxygen (oxo), $R^7$ and $R^8$ in each case represent hydrogen, $R^9$ represents phenyl, methylenedioxyphenyl or 5- or 6-membered hetaryl having 1 or 2 heteroatoms from the series consisting of nitrogen, oxygen and sulphur, which in each case can optionally be substituted up to 3 times by substituents of the group: fluorine, chlorine, bromine, iodine, C$_1$–C$_4$-alkyl, hydroxyl, C$_1$–C$_4$-alkoxy, C$_1$–C$_4$-alkylthio, C$_1$–C$_4$-alkylcarbonyl, phenyl, phenoxy, furyl, thienyl, pyrrolyl, thiazolyl, pyridyl, furyloxy, thienyloxy, pyrrolyloxy, thiazolyloxy, pyridyloxy, C$_1$–C$_4$-alkyl substituted by fluorine or chlorine, C$_1$–C$_3$-alkoxy substituted by fluorine or chlorine, C$_1$–C$_3$-alkylthio substituted by fluorine or chlorine, C$_1$–C$_4$-alkylcarbonyl substituted by fluorine or chlorine, $R^{10}$ represents hydrogen, fluorine, C$_1$–C$_4$-alkyl or C$_1$–C$_4$-alkoxy, $R^{11}$ represents hydrogen, fluorine, chlorine, bromine or C$_1$–C$_4$-alkyl, $R^{12}$ represents hydrogen or methyl, $R^{13}$ represents hydrogen, methyl, iso-propyl, iso-butyl, sec-butyl, hydroxymethyl, 1-hydroxyethyl, mercaptomethyl, 2-methylthioethyl, 3-aminopropyl, 4-aminobutyl, carboxymethyl, 2-carboxyethyl, carbamoylmethyl, 2-carbamoylethyl, 3-guanidinopropyl, phenyl, benzyl, 4-hydroxybenzyl, 4-methoxybenzyl, 2-nitrobenzyl, 3-nitrobenzyl, 4-nitrobenzyl, 2-aminobenzyl, 3-aminobenzyl, 4-aminobenzyl, 3,4-dichlorobenzyl, 4-iodobenzyl, α-naphthylmethyl, β-naphthylmethyl 3-indolylmethyl, 4-imidazolylmethyl, 1,2,3-triazol-1-ylmethyl, 1,2,4-triazol-1-ylmethyl, 2-pyridylmethyl or 4-pyridylmethyl, where functional groups can optionally be present in protected form, $R^{12}$ and $R^{13}$ also together represent —(CH$_2$)$_3$— or —(CH$_2$)$_4$—, and $R^{14}$ represents C$_1$–C$_4$-alkyl, benzyl or another C-terminal protective group, or a pharmaceutically acceptable salt thereof.

4. The compound of claim 1 in which $R^1$ and $R^3$ in each case represent hydrogen, fluorine, chlorine, bromine, methyl or ethyl, $R^2$ and $R^4$ in each case represent methoxy, ethoxy, trifluoromethoxy, difluoromethoxy, chlorodifluoromethoxy, 2-chloro-1,1,2-trifluoroethoxy, 1,1,2-trifluoroethoxy, 1,1,2,2-tetrafluoroethoxy, 2,2,2-trichloro-1,1-difluoromethoxy or 1,1-difluoroethoxy, $R^5$ represents hydroxyl, methylamino, ethylamino, n-propylamino, isopropylamino, n-butylamino, isobutylamino, sec-butylamino, tert-butylamino or the radical —NR$^{12}$—CHR$^{13}$—COOR$^{14}$, $R^6$ represents hydrogen, or $R^5$ and $R^6$ together represent oxygen (oxo), $R^7$ and $R^8$ in each case represent hydrogen, $R^9$ represents phenyl, methylenedioxyphenyl, furyl, thienyl, pyrrolyl, oxazolyl, isoxazolyl, thiazolyl or pyridyl, which in each case can optionally be mono-substituted or disubstituted by substituents of the group fluorine, chlorine, bromine, iodine, methyl, ethyl, n-propyl, isopropyl, n-butyl, isobutyl, sec-butyl, tert-butyl, trifluoromethyl, difluoromethyl, chlorodifluoromethyl, 2-chloro-1,1,2-trifluoroethyl, 1,1,2-trifluoroethyl, 1,1,2,2-tetrafluoroethyl, 1,1-difluoro-2,2,2-trichloroethyl, 2,2,2-trifluoroethyl, 1,1,2,3,3,3-hexafluoropropyl, 2,2,3,3-tetrafluoropropyl, 2,2,3,3,3-pentafluoropropyl, hydroxyl, methoxy, ethoxy, n-propoxy, isopropoxy, n-butoxy, isobutoxy, sec-butoxy, tert-butoxy, trifluoromethoxy, difluoromethoxy, chlorodifluoromethoxy, 2-chloro-1,1,2-trifluoroethyl, 1,1,2-trifluoroethoxy, 1,1,2,2-tetrafluoroethoxy, 2,2,2-trichloro-1,1-difluoromethoxy, 1,1-difluoroethoxy, methylthio, ethylthio, trifluoromethylthio, 1,1-difluoroethylthio, 2,2,2-trifluoroethylthio, phenyl, phenoxy, furyl, thienyl, pyrrolyl, thiazolyl, pyridyl, furyloxy, thienyloxy, pyrrolyloxy, thiazolyloxy, pyridyloxy, acetyl, propionyl, propylcarbonyl, butylcarbonyl or 2-methylpropylcarbonyl, $R^{10}$ represents hydrogen, fluorine, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy or tert-butoxy, $R^{11}$ represents hydrogen, fluorine, chlorine, bromine, methyl, ethyl, n-propyl, isopropyl, n-butyl, isobutyl, sec-butyl or tert-butyl, $R^{12}$ represents hydrogen, $R^{13}$ represents hydrogen, methyl, iso-propyl, iso-butyl, sec-butyl, hydroxymethyl, 1-hydroxyethyl, mercaptomethyl, 2-methylthioethyl, 3-aminopropyl, 4-aminobutyl, carboxymethyl, 2-carboxyethyl, carbamoylmethyl, 2-carbamoylethyl, 3-guanidinopropyl, phenyl, benzyl, 4-hydroxybenzyl, 3-indolylmethyl or 4-imidazolylmethyl, and $R^{14}$ represents methyl, ethyl, n-propyl, isopropyl, n-butyl, isobutyl, sec-butyl, tert-butyl or benzyl, or a pharmaceutically acceptable salt thereof.

5. A process for the preparation of a compound of the formula (I-a)

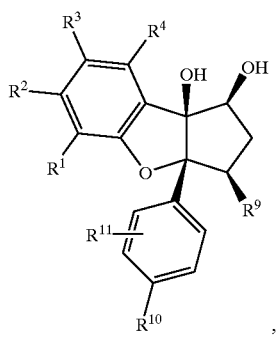

(I-a)

in which

R¹ and R³ independently of one another in each case represent hydrogen, halogen or alkyl, R² and R⁴ independently of one another in each case represent halogen, alkyl or alkoxy optionally substituted by fluorine and chlorine, R⁹ represents or hetaryl, which in each case can optionally be substituted up to four times by substituents of the group: halogen, $C_1$–$C_6$-alkyl, hydroxyl, $C_1$–$C_4$-alkoxy, $C_1$–$C_4$-alkylthio, $C_1$–$C_4$-alkylcarbonyl, phenyl, phenoxy, hetaryl, hetaryloxy, $C_1$–$C_4$-alkyl substituted by fluorine or chlorine, $C_1$–$C_4$-alkoxy substituted by fluorine or chlorine, $C_1$–$C_4$-alkylthio substituted by fluorine or chlorine, $C_1$–$C_4$-alkylcarbonyl substituted by fluorine or chlorine, R¹⁰ represents hydrogen, halogen, alkyl or alkoxy and R¹¹ represents hydrogen, halogen or alkyl, with the exception of 3,3a-dihydro-6,8-dimethoxy-3a-(4-methoxyphenyl)-3-phenyl-1H-cyclopenta[b]benzofuran-1,8b(2H)-diol, characterized in that a ketoaldehydes of the formula (II-a)

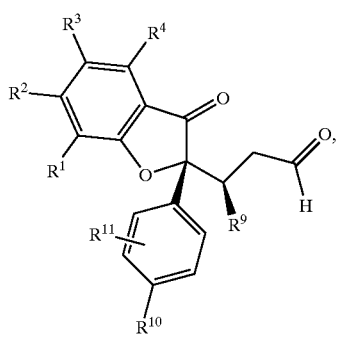

(II-a)

in which

R¹, R², R³, R⁴, R⁹, R¹⁰ and R¹¹ have the meanings as defined above, is subjected to reductive cyclization.

6. A process for the preparation of a, compound of the formula (I-b)

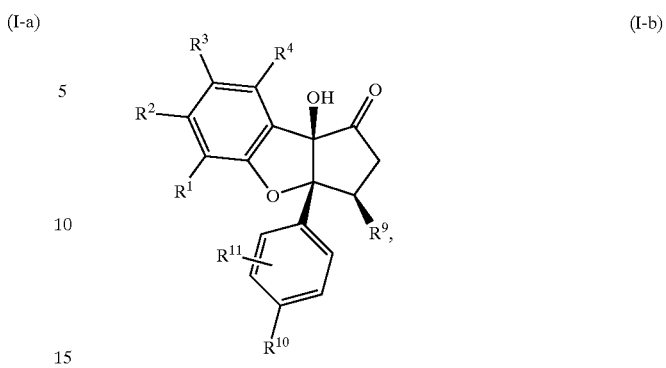

(I-b)

in which

R¹ and R³ independently of one another in each case represent hydrogen, halogen or alkyl, R² and R⁴ independently of one another in each case represent halogen, alkyl or alkoxy optionally substituted by fluorine and chlorine, R⁹ represents phenyl or hetaryl, which in each case can optionally be substituted up to four times by substituents of the group: halogen, $C_1$–$C_6$-alkyl, hydroxyl, $C_1$–$C_4$-alkoxy, $C_1$–$C_4$-alkylthio, $C_1$–$C_4$-alkylcarbonyl, phenyl, phenoxy, hetaryl, hetaryloxy, $C_1$–$C_4$-alkyl substituted by fluorine or chlorine, $C_1$–$C_4$-alkoxy substituted by fluorine or chlorine, $C_1$–$C_4$-alkylthio substituted by fluorine or chlorine, $C_1$–$C_4$-alkylcarbonyl substituted by fluorine or chlorine, R¹⁰ represents hydrogen, halogen, alkyl or alkoxy and R¹¹ represents hydrogen, halogen or alkyl, with the exception of 3,3a-dihydro-6,8-dimethoxy-3a-(4-methoxyphenyl)-3-phenyl-1H-cyclopenta[b]benzofuran-1,8b(2H)-diol, characterized in that a dihydrocyclopentabenzofurandiol of the formula (I-a)

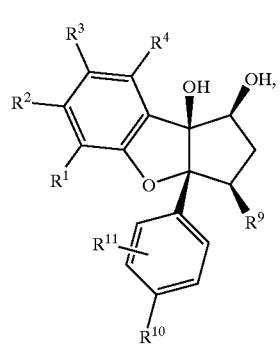

(I-a)

in which

R¹, R², R³, R⁴, R⁹, R¹⁰ and R¹¹ have the meanings as defined above, is oxidized.

7. A process for the preparation of a compound of the formula (I-d)

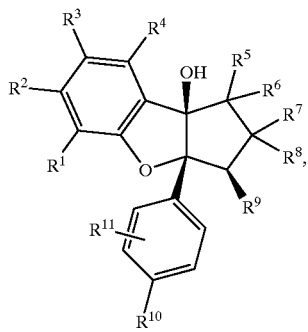

(I-d)

in which

R[1] and R[3] independently of one another in each case represent hydrogen, halogen or alkyl, R[2] and R[4] independently of one another in each case represent halogen, alkyl or alkoxy optionally substituted by fluorine and chlorine, R[5] represents hydroxyl, alkylamino or the radical —NR[12]—CHR[13]—COOR[14], in which R[12] represents hydrogen or alkyl, R[13] represents one of the radicals of a natural amino acid or represents hydrogen, ($C_1$–$C_4$)-alkyl optionally substituted by amino or hydroxyl or represents mercaptomethyl, methylthioethyl, carboxymethyl, carboxyethyl, carbamoylmethyl, carbamoylethyl, guanidinopropyl or represents phenyl or benzyl optionally substituted by amino, nitro, halogen, hydroxyl or methoxy or represents naphthylmethyl, indolylmethyl, imidazolylmethyl, triazolylmethyl or pyridylmethyl, where functional groups can optionally be present in protected form, or R[12] and R[13] together represent —(CH$_2$)$_3$— and —(CH$_2$)$_4$—, and R[14] represents alkyl, benzyl or another C-terminal protective group, R[6] represents hydrogen or R[5] and R[6] together represent oxygen (oxo), R[7] and R[8] in each case represent hydrogen, R[9] represents phenyl or hetaryl, which in each case can optionally be substituted up to four times by substituents of the group: halogen, $C_1$–$C_6$-alkyl, hydroxyl, $C_1$–$C_4$-alkoxy, $C_1$–$C_4$-alkylthio, $C_1$–$C_4$-alkylcarbonyl, phenoxy, phenoxy, hetaryl, hetaryloxy, $C_1$–$C_4$-alkyl substituted by fluorine or chlorine, $C_1$–$C_4$-alkoxy substituted by fluorine or chlorine, $C_1$–$C_4$-alkylthio substituted by fluorine or chlorine, $C_1$–$C_4$-alkylcarbonyl substituted by fluorine or chlorine, R[10] represents hydrogen, halogen, alkyl or alkoxy and R[11] represents hydrogen, halogen or alkyl, with the restriction that at least one of the radicals R[1], R[3] and R[11] represents halogen or alkyl, characterized in that this radical or these radicals are introduced by electrophilic aromatic substitution of acompound of the formula (I) of claim 1

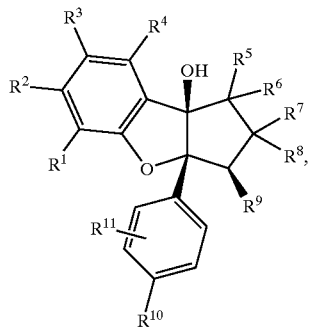

(I)

where R[1] to R[11] are as defined in claim 13, in which the radical or radicals to be substituted represent(s) hydrogen.

8. A process for the preparation of a compounds of the formula (I-e)

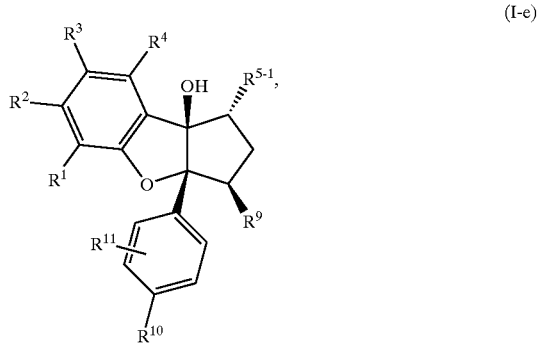

(I-e)

in which

R[1] and R[3] independently of one another in each case represent hydrogen, halogen or alkyl, R[2] and R[4] independently of one another in each case represent halogen, alkyl or alkoxy optionally substituted by fluorine and chlorine, R[9] represents phenyl or hetaryl, which in each case can optionally be substituted up to four times by substituents of the group: halogen, $C_1$–$C_6$-alkyl, hydroxyl, $C_1$–$C_4$-alkoxy, $C_1$–$C_4$-alkylthio, $C_1$–$C_4$-alkylcarbonyl, phenyl, phenoxy, hetaryl, hetaryloxy, $C_1$–$C_4$-alkyl substituted by fluorine or chlorine, $C_1$–$C_4$-alkoxy substituted by fluorine or chlorine, $C_1$–$C_4$-alkylthio substituted by fluorine or chlorine, $C_1$–$C_4$-alkylcarbonyl substituted by fluorine or chlorine.

R[10] represents hydrogen, halogen, alkyl or alkoxy and

R[11] represents hydrogen, halogen or alkyl,

R[5-1] represents alkylamino or the radical —NR[12]—CHR[13]—COOR[14], in which

R[12] represents hydrogen or alkyl,

R[13] represents one of the radicals of a natural amino acid or represents hydrogen, ($C_1$–$C_4$)-alkyl option ally substituted by amino or hydroxyl or represents mercaptomethyl, methylthioethyl, carboxymethyl, carboxyethyl, carbamoylmethyl, carbamoylethyl, guanidinopropyl or represents phenyl or benzyl optionally substituted by amino, nitro, halogen, hydroxyl or methoxy or represents naphthylmethyl, indolylmethyl, imidazolylmethyl, triazolylmethyl or pyridylmethyl, where functional groups can optionally be present in protected form, or $R^{12}$ and $R^{13}$ together represent —$(CH_2)_3$— and —$(CH_2)_4$—, and $R^{14}$ represents alkyl, benzyl or another C-terminal protective group, characterized in that a tetrahydrocyclopentabenzofuranone of the formula (I-b)

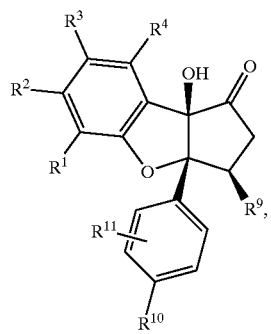

(I-b)

in which $R^1$ to $R^4$ and $R^9$ to $R^{11}$ have the meanings as defined above, is reacted with primary amines or amino acid derivatives of the formula (III)

$$H-R^{5-1} \qquad (III)$$

in which $R^{5-1}$ represents alkylamino or the radical —$NR^{12}$—$CHR^{13}$—$COOR^{14}$, in which $R^{12}$, $R^{13}$ and $R^{14}$ have the meanings as defined above, in the presence of a reducing agent.

9. A pharmaceutical composition comprising one or more cyclopentafuran compounds of the formula (I)

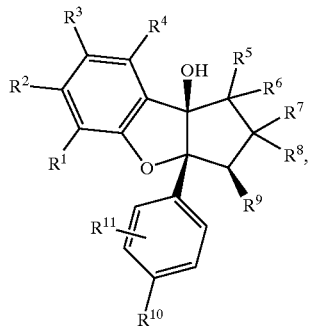

(I)

in which $R^1$ and $R^3$ independently of one another in each case represent hydrogen, halogen or alkyl, $R^2$ and $R^4$ independently of one another in each case represent halogen, alkyl or alkoxy optionally substituted by fluorine and chlorine, $R^5$ represents hydroxyl, alkylamino or the radical —$NR^{12}$—$CHR^{13}$—$COOR^{14}$, in which $R^{12}$ represents hydrogen or alkyl, $R^{13}$ represents one of the radicals of a natural amino acid or represents hydrogen, ($C_1$–$C_4$)-alkyl optionally substituted by amino or hydroxyl or represents mercaptomethyl, methylthioethyl, carboxymethyl, carboxyethyl, carbamoylmethyl, carbamoylethyl, guanidinopropyl or represents phenyl or benzyl optionally substituted by amino, nitro, halogen, hydroxyl or methoxy or represents naphthylmethyl, indolylmethyl, imidazolylmethyl, triazolylmethyl or pyridylmethyl, where functional groups can optionally be present in protected form, or $R^{12}$ and $R^{13}$ together represent —$(CH_2)_3$— and —$(CH_2)4$—, and $R^{14}$ represents alkyl, benzyl or another C-terminal protective group, $R^6$ represents hydrogen or $R^5$ and $R^6$ together represent oxygen (oxo), $R^7$ and $R^8$ in each case represent hydrogen, $R^9$ represents phenyl or hetaryl, which in each case can optionally be substituted up to four times by substituents of the group: halogen, $C_1$–$C_6$-alkyl, hydroxyl, $C_1$–$C_4$-alkoxy, $C_1$–$C_4$-alkylthio, $C_1$–$C_4$-alkylcarbonyl, phenyl, phenoxy, hetaryl, hetaryloxy, $C_1$–$C_4$-alkyl substituted by fluorine or chlorine, $C_1$–$C_4$-alkoxy substituted by fluorine or chlorine, $C_1$–$C_4$-alkylthio substituted by fluorine or chlorine, $C_1$–$C_4$-alkylcarbonyl substituted by fluorine or chlorine, $R^{10}$ represents hydrogen, halogen, alkyl or alkoxy and $R^{11}$ represents hydrogen, halogen or alkyl, or a pharmaceutically acceptable salt thereof.

* * * * *

SEQUENCE LISTING

<160> NUMBER OF SEQ ID NOS: 2

<210> SEQ ID NO 1
<211> LENGTH: 34
<212> TYPE: DNA
<213> ORGANISM: Homo sapiens

-continued

```
<400> SEQUENCE: 1
tccctcgaga tctcccagag gcaaactgcc agat                    34

<210> SEQ ID NO 2
<211> LENGTH: 36
<212> TYPE: DNA
<213> ORGANISM: Homo sapiens

<400> SEQUENCE: 2
tcctcgagcc atggctacca gttgggcggc gagatc                  36
```